US012808887B2

(12) United States Patent
Dooley et al.

(10) Patent No.: US 12,808,887 B2
(45) Date of Patent: Nov. 24, 2026

(54) CHOLESTEROL ASSAYS FOR QUANTIFYING EXTRACELLULAR VESICLES

(71) Applicant: LONZA SALES AG, Basel (CH)

(72) Inventors: Kevin P. Dooley, Boston, MA (US); Aaron J. Sulentic, Boston, MA (US); Shelly A. Martin, Stoneham, MA (US); David Lechner, Cambridge, MA (US); Charlotte M. Piard, Cambridge, MA (US); Joon Chong Yee, Acton, MA (US); Leila Albers, Braintree, MA (US)

(73) Assignee: LONZA SALES AG, Basel (CH)

( * ) Notice: Subject to any disclaimer, the term of this patent is extended or adjusted under 35 U.S.C. 154(b) by 993 days.

(21) Appl. No.: 17/793,629

(22) PCT Filed: Jan. 15, 2021

(86) PCT No.: PCT/US2021/013722

§ 371 (c)(1),
(2) Date: Sep. 5, 2023

(87) PCT Pub. No.: WO2021/146616

PCT Pub. Date: Jul. 22, 2021

(65) Prior Publication Data

US 2023/0184791 A1 Jun. 15, 2023

Related U.S. Application Data

(60) Provisional application No. 63/047,159, filed on Jul. 1, 2020, provisional application No. 62/962,691, filed on Jan. 17, 2020.

(51) Int. Cl.
*G01N 33/92* (2006.01)

(52) U.S. Cl.
CPC .................................... *G01N 33/92* (2013.01)

(58) Field of Classification Search
CPC ............................... G01N 33/92; G01N 33/53
See application file for complete search history.

(56) References Cited

U.S. PATENT DOCUMENTS 10,195,290 B1 2/2019 Dooley et al.
2018/0371418 A1* 12/2018 Yang .................... C12N 5/0665

FOREIGN PATENT DOCUMENTS

EP 3483588 A1 5/2019
WO 2009/105044 A1 8/2009
WO 2019/040920 A1 2/2019
WO 2019/060629 A1 3/2019

(Continued)

OTHER PUBLICATIONS

He et al, "Direct Exosome Quantification via Bivalent-Cholesterol-Labeled DNA Anchor for Signal Amplification" Anal. Chem. 2017, 89, 12968â12975 (Year: 2017).*

(Continued)

*Primary Examiner* — Dennis White
(74) *Attorney, Agent, or Firm* — MEDLER FERRO WOODHOUSE & MILLS PLLC

(57) ABSTRACT

Provided herein are methods of quantifying extracellular vesicle concentration, such as exosomes, by measuring cholesterol content in a sample. Also provided are methods (Continued)

of processing extracellular vesicles to remove non-exosomal species which contain cholesterol.

18 Claims, 18 Drawing Sheets

Specification includes a Sequence Listing.

(56) References Cited

FOREIGN PATENT DOCUMENTS

| | | | |
|---|---|---|---|
| WO | 2019/099942 | A1 | 5/2019 |
| WO | 2019/133934 | A2 | 7/2019 |
| WO | 2020/101740 | A1 | 5/2020 |
| WO | 2021/030777 | A1 | 2/2021 |

OTHER PUBLICATIONS

Kim et al, "Cardiac-specific delivery by cardiac tissue-targeting peptide-expressing exosomes", Biochemical and Biophysical Research Communications 499 (2018) 803-808. (Year: 2018).*

Morton et al, "MARCKS-ED Peptide as a Curvature and Lipid Sensor", ACS Chem. Biol. 2013, 8, 1, 218â225. (Year: 2013).*

Yu et al, "Pancreatic cancer-derived exosomes promote tumor metastasis and liver pre-metastatic niche formation", Oncotarget. Jun. 28, 2017;8(38):63461â63483. (Year: 2017).*

Hartjes, T.A. et al., "Extracellular Vesicle Quantification and Characterization: Common Methods and Emerging Approaches", Bioengineering 6(7):1-26 (2019).

He, F. et al., "Direct Exosome Quantification via Bivalent-Choleserol-Labeled DNA Anchor for Signal Amplification", Analytical Chemistry 89(23):12968-12975 (2017).

Kuypers, F.A. et al., "Survival of rabbit and horse erythrocytes in vivo after changing the fatty acyl composition of their phosphatidylcholine", Biochimica et Biophysica Acta 819:170-178 (1985).

Mei, B. et al., "Rational design of a fully active, long-acting PEGylated factor VIII for hemophilia A treatment", Blood 116(2):270-279 (2010).

Möbius, W. et al., "Immunoelectron microscopic localization of cholesterol using biotinylated and non-cytolytic perfringolysin O", Journal of Histochemistry and Cytochemistry 50(1):43-55 (2002).

Parolini, I. et al., "Microenvironmental pH Is a Key Factor for Exosome Traffic in Tumor Cells", Journal of Biological Chemistry 284(49):34211-34222 (2009).

Skočaj, M. et al., "Characterisation of plasmalemmal shedding of vesicles induced by the cholesterol/sphingomyelin binding protein, ostreolysin A-mCherry", Biochimica et Biophysica Acta (BBA)—Biomembranes 1858(11):2882-2893 (2016).

Stremersch, S. et al., "Comparing exosome-like vesicles with liposomes for the functional delivery of small RNAs", Journal of Controlled Release 232(9):51-61 (2016).

* cited by examiner

F1 HPLC Lipid Analysis

| Lipid | |
|---|---|
| PC | Phosphatidylcholine |
| PE | Phosphatidylethanolamine |
| PS | Phosphatidylserine |
| PG | Phosphatidylglycerol |
| PI | Phosphatidylinositol |
| Cer | Cerimide |
| SM | Sphingomyelin |
| Chol | Cholesterol |
| L | Lyso- |

SEQUENCE LISTING

```
<160> NUMBER OF SEQ ID NOS: 1

<210> SEQ ID NO 1
<211> LENGTH: 879
<212> TYPE: PRT
<213> ORGANISM: Artificial Sequence
<220> FEATURE:
<223> OTHER INFORMATION: Prostaglandin F2 Receptor Inhibitor

<400> SEQUENCE: 1

Met Gly Arg Leu Ala Ser Arg Pro Leu Leu Leu Ala Leu Leu Ser Leu
1               5                   10                  15

Ala Leu Cys Arg Gly Arg Val Val Arg Val Pro Thr Ala Thr Leu Val
            20                  25                  30

Arg Val Val Gly Thr Glu Leu Val Ile Pro Cys Asn Val Ser Asp Tyr
        35                  40                  45

Asp Gly Pro Ser Glu Gln Asn Phe Asp Trp Ser Phe Ser Ser Leu Gly
    50                  55                  60

Ser Ser Phe Val Glu Leu Ala Ser Thr Trp Glu Val Gly Phe Pro Ala
65                  70                  75                  80

Gln Leu Tyr Gln Glu Arg Leu Gln Arg Gly Glu Ile Leu Leu Arg Arg
                85                  90                  95

Thr Ala Asn Asp Ala Val Glu Leu His Ile Lys Asn Val Gln Pro Ser
            100                 105                 110

Asp Gln Gly His Tyr Lys Cys Ser Thr Pro Ser Thr Asp Ala Thr Val
        115                 120                 125

Gln Gly Asn Tyr Glu Asp Thr Val Gln Val Lys Val Leu Ala Asp Ser
    130                 135                 140

Leu His Val Gly Pro Ser Ala Arg Pro Pro Pro Ser Leu Ser Leu Arg
145                 150                 155                 160

Glu Gly Glu Pro Phe Glu Leu Arg Cys Thr Ala Ala Ser Ala Ser Pro
                165                 170                 175

Leu His Thr His Leu Ala Leu Leu Trp Glu Val His Arg Gly Pro Ala
            180                 185                 190

Arg Arg Ser Val Leu Ala Leu Thr His Glu Gly Arg Phe His Pro Gly
        195                 200                 205

Leu Gly Tyr Glu Gln Arg Tyr His Ser Gly Asp Val Arg Leu Asp Thr
    210                 215                 220

Val Gly Ser Asp Ala Tyr Arg Leu Ser Val Ser Arg Ala Leu Ser Ala
225                 230                 235                 240

Asp Gln Gly Ser Tyr Arg Cys Ile Val Ser Glu Trp Ile Ala Glu Gln
                245                 250                 255

Gly Asn Trp Gln Glu Ile Gln Glu Lys Ala Val Glu Val Ala Thr Val
            260                 265                 270

Val Ile Gln Pro Ser Val Leu Arg Ala Ala Val Pro Lys Asn Val Ser
        275                 280                 285

Val Ala Glu Gly Lys Glu Leu Asp Leu Thr Cys Asn Ile Thr Thr Asp
    290                 295                 300

Arg Ala Asp Asp Val Arg Pro Glu Val Thr Trp Ser Phe Ser Arg Met
305                 310                 315                 320

Pro Asp Ser Thr Leu Pro Gly Ser Arg Val Leu Ala Arg Leu Asp Arg
                325                 330                 335

Asp Ser Leu Val His Ser Ser Pro His Val Ala Leu Ser His Val Asp
            340                 345                 350

Ala Arg Ser Tyr His Leu Leu Val Arg Asp Val Ser Lys Glu Asn Ser
```

-continued

```
        355                 360                 365

Gly Tyr Tyr Tyr Cys His Val Ser Leu Trp Ala Pro Gly His Asn Arg
    370                 375                 380

Ser Trp His Lys Val Ala Glu Ala Val Ser Ser Pro Ala Gly Val Gly
385                 390                 395                 400

Val Thr Trp Leu Glu Pro Asp Tyr Gln Val Tyr Leu Asn Ala Ser Lys
                405                 410                 415

Val Pro Gly Phe Ala Asp Asp Pro Thr Glu Leu Ala Cys Arg Val Val
            420                 425                 430

Asp Thr Lys Ser Gly Glu Ala Asn Val Arg Phe Thr Val Ser Trp Tyr
        435                 440                 445

Tyr Arg Met Asn Arg Arg Ser Asp Asn Val Val Thr Ser Glu Leu Leu
    450                 455                 460

Ala Val Met Asp Gly Asp Trp Thr Leu Lys Tyr Gly Glu Arg Ser Lys
465                 470                 475                 480

Gln Arg Ala Gln Asp Gly Asp Phe Ile Phe Ser Lys Glu His Thr Asp
                485                 490                 495

Thr Phe Asn Phe Arg Ile Gln Arg Thr Thr Glu Glu Asp Arg Gly Asn
            500                 505                 510

Tyr Tyr Cys Val Val Ser Ala Trp Thr Lys Gln Arg Asn Asn Ser Trp
        515                 520                 525

Val Lys Ser Lys Asp Val Phe Ser Lys Pro Val Asn Ile Phe Trp Ala
    530                 535                 540

Leu Glu Asp Ser Val Leu Val Val Lys Ala Arg Gln Pro Lys Pro Phe
545                 550                 555                 560

Phe Ala Ala Gly Asn Thr Phe Glu Met Thr Cys Lys Val Ser Ser Lys
                565                 570                 575

Asn Ile Lys Ser Pro Arg Tyr Ser Val Leu Ile Met Ala Glu Lys Pro
            580                 585                 590

Val Gly Asp Leu Ser Ser Pro Asn Glu Thr Lys Tyr Ile Ile Ser Leu
        595                 600                 605

Asp Gln Asp Ser Val Val Lys Leu Glu Asn Trp Thr Asp Ala Ser Arg
    610                 615                 620

Val Asp Gly Val Val Leu Glu Lys Val Gln Glu Asp Glu Phe Arg Tyr
625                 630                 635                 640

Arg Met Tyr Gln Thr Gln Val Ser Asp Ala Gly Leu Tyr Arg Cys Met
                645                 650                 655

Val Thr Ala Trp Ser Pro Val Arg Gly Ser Leu Trp Arg Glu Ala Ala
            660                 665                 670

Thr Ser Leu Ser Asn Pro Ile Glu Ile Asp Phe Gln Thr Ser Gly Pro
        675                 680                 685

Ile Phe Asn Ala Ser Val His Ser Asp Thr Pro Ser Val Ile Arg Gly
    690                 695                 700

Asp Leu Ile Lys Leu Phe Cys Ile Ile Thr Val Glu Gly Ala Ala Leu
705                 710                 715                 720

Asp Pro Asp Asp Met Ala Phe Asp Val Ser Trp Phe Ala Val His Ser
                725                 730                 735

Phe Gly Leu Asp Lys Ala Pro Val Leu Leu Ser Ser Leu Asp Arg Lys
            740                 745                 750

Gly Ile Val Thr Thr Ser Arg Arg Asp Trp Lys Ser Asp Leu Ser Leu
        755                 760                 765

Glu Arg Val Ser Val Leu Glu Phe Leu Leu Gln Val His Gly Ser Glu
    770                 775                 780
```

-continued

```
Asp Gln Asp Phe Gly Asn Tyr Tyr Cys Ser Val Thr Pro Trp Val Lys
785                 790                 795                 800

Ser Pro Thr Gly Ser Trp Gln Lys Glu Ala Glu Ile His Ser Lys Pro
                805                 810                 815

Val Phe Ile Thr Val Lys Met Asp Val Leu Asn Ala Phe Lys Tyr Pro
            820                 825                 830

Leu Leu Ile Gly Val Gly Leu Ser Thr Val Ile Gly Leu Leu Ser Cys
        835                 840                 845

Leu Ile Gly Tyr Cys Ser Ser His Trp Cys Cys Lys Lys Glu Val Gln
    850                 855                 860

Glu Thr Arg Arg Glu Arg Arg Arg Leu Met Ser Met Glu Met Asp
865                 870                 875
```

CHOLESTEROL ASSAYS FOR QUANTIFYING EXTRACELLULAR VESICLES

CROSS-REFERENCE TO RELATED APPLICATIONS

This application claims priority benefit of U.S. Provisional Application Nos. 62/962,691, filed Jan. 17, 2020; and 63/047,159, filed Jul. 1, 2020, each of which is herein incorporated by reference in its entirety.

REFERENCE TO SEQUENCE LISTING SUBMITTED ELECTRONICALLY VIA EFS-WEB

The content of the electronically submitted sequence listing in ASCII text file (Name: 4000_080PC02_Seqlisting_ST25.txt; Size: 7,901 bytes; and Date of Creation: Jan. 14, 2021), filed with the application, is incorporated herein by reference in its entirety.

FIELD OF DISCLOSURE

The present disclosure relates to methods of quantifying extracellular vesicles (EVs), e.g., exosomes, by quantifying their cholesterol concentration. The present disclosure is also related to preparing a sample for cholesterol analysis by removing other cholesterol-containing contaminants.

BACKGROUND

Extracellular vesicles (EVs) (e.g., exosomes) are important mediators of intercellular communication. They are produced by nearly every eukaryotic cell and comprise a membrane and an internal space (i.e., lumen), which is enclosed by the membrane. Depending on the cells from which they are produced, EVs can comprise different lipids, proteins, carbohydrates, and/or nucleic acids. As drug delivery vehicles, EVs (e.g., exosomes) offer many advantages over traditional drug delivery methods as a new treatment modality in many therapeutic areas. However, the ability to reliably quantify EVs (e.g., exosomes) is an important challenge to their development for therapeutic and diagnostic purposes. The current methods available for quantifying EVs (e.g., exosomes) are time consuming and generally require techniques such as nanoparticle tracking analysis (NTA) that do not have a clear path to scalability in manufacturing. Therefore, there remains a need for methods that can provide for more rapid and efficient means of quantifying EVs (e.g., exosomes) from a sample.

SUMMARY OF THE DISCLOSURE

The methods of the present disclosure are related to preparing a sample comprising one or more extracellular vesicles, the methods comprising quantifying the concentration of extracellular vesicles in a sample by analyzing a cholesterol content of the sample. In some aspects, the cholesterol content is correlated with the concentration of extracellular vesicles. In some aspects, the method further comprising processing the sample using filtration, ultracentrifugation, or polyethylene glycol (PEG) precipitation. In some aspects, the sample is prepared prior to the analysis. In some aspects, the sample is prepared from a bioreactor. In some aspects, the extracellular vesicles are produced in a mixture comprising a cell. In some aspects, the extracellular vesicles are produced in a mixture comprising a cell, which is a HEK293 cell, a Chinese hamster ovary (CHO) cell, a mesenchymal stem cell (MSC), a fibroblast cell, a s9f cell, a fHDF fibroblast cell, an AGE.HN neuronal precursor cell, a CAP amniocyte cell, an adipose mesenchymal stem cell, an RPTEC/TERT1 cell, or any combination thereof. In some aspects, the cells have viability of at least about 80%, at least about 85%, at least about 90%, at least about 95%, or about 100%. In some aspects, the cells have a viability of at least about 90%. In some aspects, the sample is prepared from any purification process. In some aspects, the sample is filtered using filtration or tangential flow filtration (TFF).

In some aspects, the sample is filtered using a 0.45 μm filter or a 0.2 μm filter. In some aspects, the sample is prepared using ultracentrifugation. In some aspects, the sample is prepared using density gradient ultracentrifugation (e.g., sucrose, iodixanol). In some aspects, the sample is prepared using PEG precipitation. In some aspects, the cholesterol content is analyzed using a fluorometric method to detect the cholesterol. In some aspects, the cholesterol content is analyzed using an AMPLEX Red Cholesterol Assay Kit. In some aspects, the concentration of cholesterol analyzed is less than about 0.05 μg/mL, less than about 0.1 μg/mL, less than about 0.2 μg/mL, less than about 0.3 μg/mL, less than about 0.5 μg/mL, less than about 1 μg/mL, less than about 20 μg/mL, less than about 3 μg/mL, less than about 40 μg/mL, less than about 5 μg/mL, less than about 10 μg/mL, less than about 50 μg/mL, less than about 100 μg/mL, less than about 200 μg/mL, less than about 300 μg/mL, less than about 400 μg/mL, less than about 500 μg/mL, less than about 600 μg/mL, less than about 700 μg/mL, less than about 800 μg/mL, less than about 900 μg/mL, less than about 1000 μg/mL, less than about 1500 μg/mL, less than about 2000 μg/mL, less than about 2500 μg/mL, or less than about 3000 μg/mL.

In some aspects, the concentration of cholesterol analyzed is less than about 100 μg/mL. In some aspects, the cholesterol content is analyzed in cell culture. In some aspects, the cell culture is perfusion cell culture or fed-batch cell culture. In some aspects, the cholesterol content is analyzed by collecting cellular supernatant. In some aspects, the cellular supernatant is collected and analyzed at least once per day.

In some aspects, the cellular supernatant is collected and analyzed for a period of about 1-90 days. In some aspects, the extracellular vesicles are engineered extracellular vesicles. In some aspects, the extracellular vesicles comprise a scaffold protein. In some aspects, the extracellular vesicles comprise a Scaffold X protein. In some aspects, the Scaffold X is selected from the group consisting of prostaglandin F2 receptor negative regulator (the PTGFRN protein); basigin (the BSG protein); immunoglobulin superfamily member 2 (the IGSF2 protein); immunoglobulin superfamily member 3 (the IGSF3 protein); immunoglobulin superfamily member 8 (the IGSF8 protein); integrin beta-1 (the ITGB1 protein); integrin alpha-4 (the ITGA4 protein); 4F2 cell-surface antigen heavy chain (the SLC3A2 protein); a class of ATP transporter proteins (the ATP1A1, ATP1A2, ATP1A3, ATP1A4, ATP1B3, ATP2B1, ATP2B2, ATP2B3, ATP2B4 proteins); a functional fragment thereof; and any combination thereof.

In some aspects, the Scaffold X is PTGFRN protein or a functional fragment thereof. In some aspects, the Scaffold X comprises an amino acid sequence as set forth in SEQ ID NO: 1. In some aspects, the Scaffold X comprises an amino acid sequence at least 50%, at least 60%, at least 70%, at least 80%, at least 85%, at least 90%, at least 95%, at least 96%, at least 97%, at least 98%, at least 99%, or about 100% identical to SEQ ID NO: 1.

In some aspects, the extracellular vesicles comprise a Scaffold Y protein. In some aspects, the Scaffold Y protein is selected from the group consisting of myristoylated alanine rich Protein Kinase C substrate (the MARCKS protein), myristoylated alanine rich Protein Kinase C substrate like 1 (the MARCKSL1 protein), brain acid soluble protein 1 (the BASP1 protein), a functional fragment thereof, and any combination thereof. In some aspects, the Scaffold Y is a BASP1 protein or a functional fragment thereof. In some aspects, the Scaffold Y comprises an N terminus domain (ND) and an effector domain (ED), wherein the ND and/or the ED are associated with the luminal surface of the EV. In some aspects, the ND is associated with the luminal surface of the extracellular vesicles via myristoylation. In some aspects, the ED is associated with the luminal surface of the extracellular vesicles by an ionic interaction. In some aspects, the ED comprises (i) a basic amino acid or (ii) two or more basic amino acids in sequence, wherein the basic amino acid is selected from the group consisting of Lys, Arg, His, and any combination thereof. In some aspects, the basic amino acid is (Lys)n, wherein n is an integer between 1 and 10. In some aspects, the extracellular vesicles comprise a protein, a peptide, a small molecule, a nucleotide, a polynucleotide, an oligonucleotide, a virus or any combination thereof.

In some aspects, the extracellular vesicles comprise an antibody or an antigen binding fragment thereof, a fusion protein, an oligonucleotide, a dinucleotide, an mRNA, a virus, or any combination thereof. In some aspects, the extracellular vesicles comprise IL-2, IL-7, IL-12, CD40 L, FLT3 L, or any combination thereof. In some aspects, the extracellular vesicles comprises an oligonucleotide targeting STATS, STATE, NRas, KRas, or CEBP/β. In some aspects, the extracellular vesicles comprises a dinucleotide comprising a STING agonist. In some aspects, the cholesterol content is compared to a reference nanoparticle tracking analysis (NTA) particle count curve to generate the cholesterol concentration standard curve and the NTA particle count curve, comparing the data sets generated by each curve, and correlating NTA particle counts to cholesterol concentrations.

The methods of the present disclosure are also related to a method of preparing a cholesterol concentration standard curve to determine the concentration of extracellular vesicles in a sample based on a reference nanoparticle tracking analysis (NTA) particle count curve, comprising generating the cholesterol concentration standard curve and the NTA particle count curve, comparing the data sets generated by each curve, and correlating NTA particle counts to cholesterol concentrations. In some aspects, the extracellular vesicles are exosomes.

DETAILED DESCRIPTION OF THE DISCLOSURE

Figure 1A:
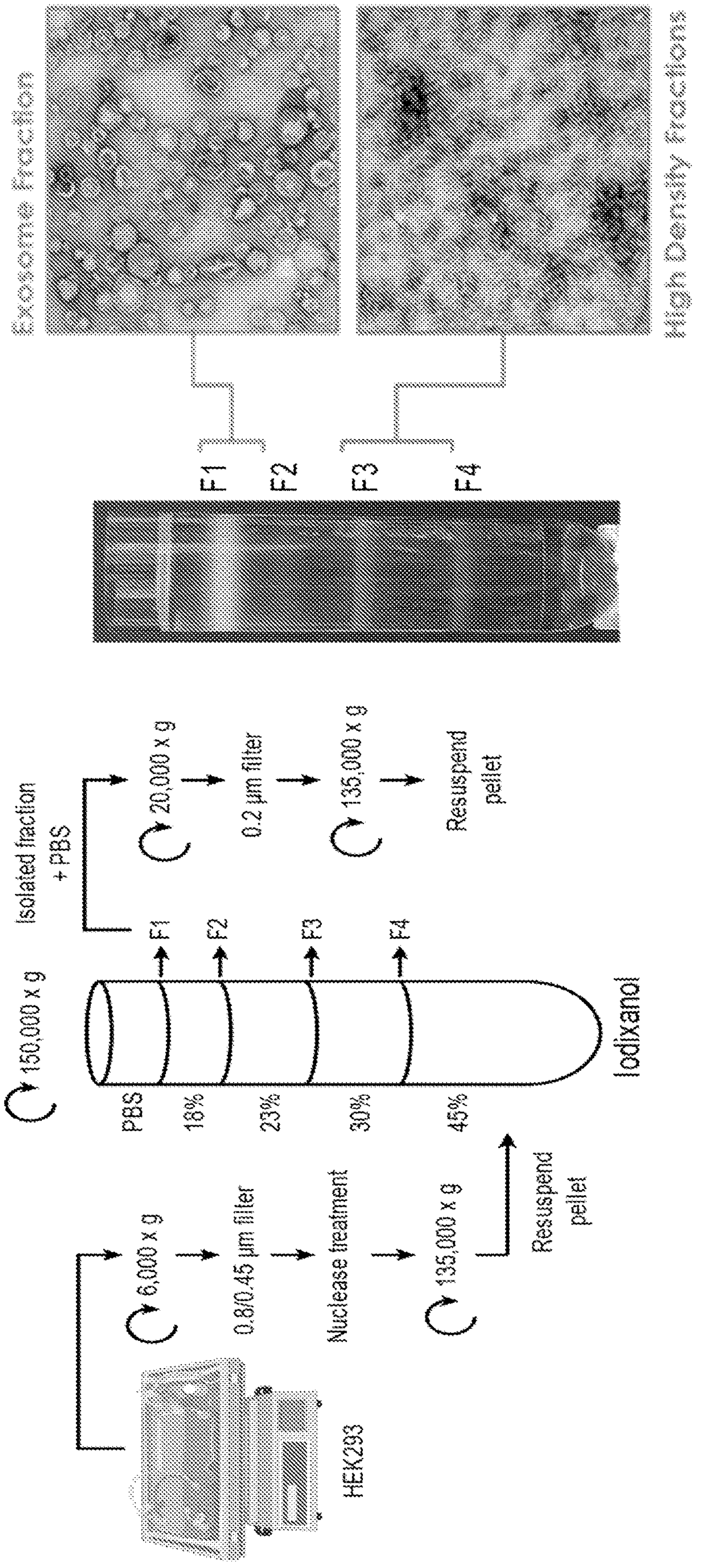
FIG. 1A shows a density gradient ultracentrifugation process diagram, and a density gradient separation of crude ultracentrifuged cell culture supernatant and identification of four individual fractions, with sample microscopy images of the F1 and F3/F4 fractions.

The present disclosure is directed to methods of quantitating extracellular vesicles in cell culture supernatant by measuring cholesterol content to quantify the extracellular vesicle count. The methods of the disclosure comprise processing a sample to remove non-extracellular vesicle species in cell culture supernatant, which contains cholesterol via various methods including 0.45 μm or 0.2 μm filtration, ultracentrifugation, and/or polyethylene glycol (PEG) precipitation.

I. Definitions

It is noted that, as used herein and in the appended claims, the singular forms "a," "an," and "the" include plural referents unless the context clearly dictates otherwise. As such, the terms "a" (or "an"), "one or more," and "at least one" can be used interchangeably herein. It is further noted that the claims can be drafted to exclude any optional element. As such, this statement is intended to serve as antecedent basis for use of such exclusive terminology as "solely," "only" and the like in connection with the recitation of claim elements, or use of a negative limitation.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Thus, ranges recited herein are understood to be shorthand for all of the values within the range, inclusive of the recited endpoints. For example, a range of 1 to 10 is understood to include any number, combination of numbers, or sub-range from the group consisting of 1, 2, 3, 4, 5, 6, 7, 8, 9, and 10.

Where a value is explicitly recited, it is to be understood that values which are about the same quantity or amount as the recited value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Nucleotides are referred to by their commonly accepted single-letter codes. Unless otherwise indicated, nucleotide sequences are written left to right in 5' to 3' orientation. Nucleotides are referred to herein by their commonly known one-letter symbols recommended by the IUPAC-IUB Biochemical Nomenclature Commission. Accordingly, A represents adenine, C represents cytosine, G represents guanine, T represents thymine, and U represents uracil.

Amino acid sequences are written left to right in amino to carboxy orientation. Amino acids are referred to herein by either their commonly known three letter symbols or by the one-letter symbols recommended by the IUPAC-IUB Biochemical Nomenclature Commission.

The term "about" or "approximately" is used herein to mean approximately roughly, around, or in the region of. When the term "about" is used in conjunction with a numerical range, it modifies that range by extending the boundaries above and below the numerical values set forth. The term used herein means within 5% of the referenced amount, e.g., about 50% is understood to encompass a range of values from 47.5% to 52.5%.

As used herein, the term "light scattering" refers to scattering and/or reflection of a light source from a focal beam. In some aspects, the light scattering can be detected at a single angle from the source (e.g., 90 degrees), or can be detected at multiple angles (e.g., in the case of multi-angle light scattering). In some aspects, the light source is a laser. In some aspects, the light source is at a wavelength in the ultraviolet spectrum, the visual spectrum, the infrared spectrum, or combinations thereof. In some aspects, the light scattering is elastic. In some aspects, the light scattering is inelastic. In some preferred aspects, the light scattering is Rayleigh (elastic) light scattering.

As used herein, the term "extracellular vesicle" or "EV" refers to a cell-derived vesicle comprising a membrane that encloses an internal space. Extracellular vesicles comprise all membrane-bound vesicles (e.g., exosomes, nanovesicles) that have a smaller diameter than the cell from which they are derived. In some aspects, extracellular vesicles range in diameter from 20 nm to 1000 nm, and can comprise various macromolecular payload either within the internal space (i.e., lumen), displayed on the external surface of the extracellular vesicle, and/or spanning the membrane. In some aspects, the payload can comprise nucleic acids, proteins, carbohydrates, lipids, small molecules, and/or combinations thereof. In certain aspects, an extracellular vehicle comprises a scaffold moiety. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, prokaryotic or eukaryotic cells, and/or cultured cells. In some aspects, the extracellular vesicles are produced by cells that express one or more transgene products.

As used herein, the term "exosome" refers to an extracellular vesicle with a diameter between 20-300 nm (e.g., between 40-200 nm). Exosomes comprise a membrane that encloses an internal space (i.e., lumen), and, in some aspects, can be generated from a cell (e.g., producer cell) by direct plasma membrane budding or by fusion of the late endosome with the plasma membrane. In certain aspects, an exosome comprises a scaffold moiety. As described infra, exosome can be derived from a producer cell, and isolated from the producer cell based on its size, density, biochemical parameters, or a combination thereof. In some aspects, the EVs, e.g., exosomes, of the present disclosure are produced by cells that express one or more transgene products.

As used herein, the term "nanovesicle" refers to an extracellular vesicle with a diameter between 20-250 nm (e.g., between 30-150 nm) and is generated from a cell (e.g., producer cell) by direct or indirect manipulation such that the nanovesicle would not be produced by the cell without the manipulation. Appropriate manipulations of the cell to produce the nanovesicles include but are not limited to serial extrusion, treatment with alkaline solutions, sonication, or combinations thereof. In some aspects, production of nanovesicles can result in the destruction of the producer cell. In some aspects, population of nanovesicles described herein are substantially free of vesicles that are derived from cells by way of direct budding from the plasma membrane or fusion of the late endosome with the plasma membrane. In certain aspects, a nanovesicle comprises a scaffold moiety. Nanovesicles, once derived from a producer cell, can be isolated from the producer cell based on its size, density, biochemical parameters, or a combination thereof.

As used herein the term "surface-engineered EVs, e.g., exosomes" (e.g., Scaffold X-engineered EVs, e.g., exosomes) refers to an EV, e.g., exosome, with the membrane or the surface of the EV, e.g., exosome, modified in its composition so that the surface of the engineered EV, e.g., exosome, is different from that of the EV, e.g., exosome, prior to the modification or of the naturally occurring EV, e.g., exosome. The engineering can be on the surface of the EV, e.g., exosome, or in the membrane of the EV, e.g., exosome, so that the surface of the EV, e.g., exosome, is changed. For example, the membrane is modified in its composition of a protein, a lipid, a small molecule, a carbohydrate, etc. The composition can be changed by a chemical, a physical, or a biological method or by being produced from a cell previously or concurrently modified by a chemical, a physical, or a biological method. Specifically, the composition can be changed by a genetic engineering or by being produced from a cell previously modified by genetic engineering. In some aspects, a surface-engineered EV, e.g., exosome, comprises an exogenous protein (i.e., a protein that the EV, e.g., exosome, does not naturally express) or a fragment or variant thereof that can be exposed to the surface of the EV, e.g., exosome, or can be an anchoring point (attachment) for a moiety exposed on the surface of the EV, e.g., exosome. In some aspects, a surface-engineered EV, e.g., exosome, comprises a higher expression (e.g., higher number) of a natural exosome protein (e.g., Scaffold X) or a fragment or variant thereof that can be exposed to the surface of the EV, e.g., exosome, or can be an anchoring point (attachment) for a moiety exposed on the surface of the EV, e.g., exosome.

As used herein the term "lumen-engineered exosome" (e.g., Scaffold Y-engineered exosome) refers to an EV, e.g., exosome, with the membrane or the lumen of the EV, e.g., exosome, modified in its composition so that the lumen of the engineered EV, e.g., exosome, is different from that of the EV, e.g., exosome, prior to the modification or of the naturally occurring EV, e.g., exosome. The engineering can be directly in the lumen or in the membrane of the EV, e.g., exosome so that the lumen of the EV, e.g., exosome is changed. For example, the membrane is modified in its composition of a protein, a lipid, a small molecule, a carbohydrate, etc. so that the lumen of the EV, e.g., exosome is modified. The composition can be changed by a chemical, a physical, or a biological method or by being produced from a cell previously modified by a chemical, a physical, or a biological method. Specifically, the composition can be changed by a genetic engineering or by being produced from a cell previously modified by genetic engineering. In some aspects, a lumen-engineered exosome comprises an exogenous protein (i.e., a protein that the EV, e.g., exosome does not naturally express) or a fragment or variant thereof that can be exposed in the lumen of the EV, e.g., exosome or can be an anchoring point (attachment) for a moiety exposed on the inner layer of the EV, e.g., exosome. In some aspects, a lumen-engineered EV, e.g., exosome, comprises a higher expression of a natural exosome protein (e.g., Scaffold X (e.g., a transmembrane molecule) or Scaffold Y) or a fragment or variant thereof that can be exposed to the lumen of the exosome or can be an anchoring point (attachment) for a moiety exposed in the lumen of the exosome.

As used herein, the term "scaffold moiety" refers to a molecule that can be used to anchor a compound of interest (e.g., payload) to the EV either on the luminal surface or on the exterior surface of the EV, or in some cases if the molecule spans the membrane, both. In certain aspects, a scaffold moiety comprises a synthetic molecule. In some aspects, a scaffold moiety comprises a non-polypeptide moiety. In some aspects, a scaffold moiety comprises a lipid, carbohydrate, or protein that naturally exists in the EV. In some aspects, a scaffold moiety comprises a lipid, carbohydrate, or protein that does not naturally exist in the EV. In certain aspects, a scaffold moiety is Scaffold X. In some aspects, a scaffold moiety is Scaffold Y. In further aspects, an exosome comprises both a Scaffold X and a Scaffold Y. Non-limiting examples of other scaffold moieties that can be present on the extracellular vesicles analyzed in the present disclosure include: aminopeptidase N (CD13); Neprilysin, AKA membrane metalloendopeptidase (MME); ectonucleotide pyrophosphatase/phosphodiesterase family member 1 (ENPP1); Neuropilin-1 (NRP1); CD9, CD63, CD81, PDGFR, GPI anchor proteins, lactadherin (MFGE8), LAMP2, and LAMP2B.

As used herein, the term "Scaffold X" refers to molecules that can be used to load payloads on the surface of extracellular vesicles (EVs), i.e., exosomes) and includes exosome proteins that have recently been identified. See, e.g., U.S. Pat. No. 10,195,290, which is incorporated herein by reference in its entirety. In some aspects, Scaffold X is any molecule that is expressed on the surface of an extracellular vesicle that can be used to load, attach, or associate molecules with the extracellular vesicle. Non-limiting examples of Scaffold X proteins include: prostaglandin F2 receptor negative regulator ("the PTGFRN protein"); basigin ("the BSG protein"); immunoglobulin superfamily member 2 ("the IGSF2 protein"); immunoglobulin superfamily member 3 ("the IGSF3 protein"); immunoglobulin superfamily member 8 ("the IGSF8 protein"); integrin beta-1 ("the ITGB1 protein); integrin alpha-4 ("the ITGA4 protein"); 4F2 cell-surface antigen heavy chain ("the SLC3A2 protein"); and a class of ATP transporter proteins ("the ATP1A1 protein," "the ATP1A2 protein," "the ATP1A3 protein," "the ATP1A4 protein," "the ATP1B3 protein," "the ATP2B1 protein," "the ATP2B2 protein," "the ATP2B3 protein," "the ATP2B protein"). PTGFRN, BSG, IGSF3, and IGSF8 are all type I single-pass transmembrane proteins with an N-terminus facing the extracellular/extravesicular environment and a C-terminus located in the cytoplasm/exosome lumen and contain at least two immunoglobulin V (IgV) repeats. In some aspects, a Scaffold X protein can be a whole protein or a fragment thereof (e.g., functional fragment, e.g., the smallest fragment that is capable of anchoring another moiety on the exterior surface or on the luminal surface of the EV, e.g., exosome). In some aspects, a Scaffold X can span the membrane and anchor a moiety to the external surface or the luminal surface of the EVs, e.g., exosomes.

As used herein, the term "Scaffold Y" refers to molecules that can be used to load payloads in the lumen of extracellular vesicles (EVs), i.e., exosomes, and includes exosome proteins that were newly identified within the lumen of exosomes. See, e.g., International Appl. Publ. No. WO 2019/099942 A1 published May 23, 2019 and International Appl. No. PCT/US2019/033629, filed May 22, 2019, which are incorporated herein by reference in their entireties. Non-limiting examples of Scaffold Y proteins include: myristoylated alanine rich Protein Kinase C substrate ("the MARCKS protein"); myristoylated alanine rich Protein Kinase C substrate like 1 ("the MARCKSL1 protein"); and brain acid soluble protein 1 ("the BASP1 protein"). In some aspects, a Scaffold Y protein can be a whole protein or a fragment thereof (e.g., functional fragment, e.g., the smallest fragment that is capable of anchoring a moiety to the luminal surface of the exosome). In some aspects, a Scaffold Y can anchor a moiety (e.g., antigen, adjuvant, and/or immune modulator) to the luminal surface of the EV, e.g., exosome.

As used herein, the term "fragment" of a protein (e.g., therapeutic protein, Scaffold X, Scaffold Y, etc.) refers to an amino acid sequence of a protein that is shorter than the naturally-occurring sequence, N- and/or C-terminally deleted or any part of the protein deleted in comparison to the naturally occurring protein. As used herein, the term "functional fragment" refers to a protein fragment that retains protein function. Accordingly, in some aspects, a functional fragment of a Scaffold X protein retains the ability to anchor a moiety on the luminal surface and/or on the exterior surface of the EV. Whether a fragment is a functional fragment can be assessed by any art known methods to determine the protein content of EVs including Western Blots, FACS analysis and fusions of the fragments with autofluorescent proteins like, e.g., GFP. In certain aspects, a functional fragment of a Scaffold X protein retains at least about 50%, at least about 60%, at least about 70%, at least about 80%, at least about 90% or at least about 100% of the ability, e.g., an ability to anchor a moiety, of the naturally occurring Scaffold X protein.

As used herein, the term "variant" of a molecule (e.g., functional molecule, antigen, Scaffold X, Scaffold Y) refers to a molecule that shares certain structural and functional identities with another molecule upon comparison by a method known in the art. For example, a variant of a protein can include a substitution, insertion, deletion, frameshift or rearrangement in another protein.

In some aspects, a variant of a Scaffold X comprises a variant having at least about 70% identity to the full-length, mature PTGFRN, BSG, IGSF2, IGSF3, IGSF8, ITGB1, ITGA4, SLC3A2, or ATP transporter proteins or a fragment (e.g., functional fragment) of the PTGFRN, BSG, IGSF2, IGSF3, IGSF8, ITGB1, ITGA4, SLC3A2, or ATP transporter proteins. In some aspects, variants or variants of fragments of PTGFRN share at least about 70%, at least about 80%, at least about 85%, at least about 90%, at least about 95%, at least about 96%, at least about 97%, at least about 98%, or at least about 99% sequence identity with PTGFRN according to SEQ ID NO: 1 or with a functional fragment thereof. In some aspects, the variant or variant of a fragment of Scaffold X protein disclosed herein retains the ability to be specifically anchored (or linked) to EVs. In some aspects, the Scaffold X includes one or more mutations, for example, conservative amino acid substitutions.

In some aspects, a variant of a Scaffold Y comprises a variant having at least 70% identity to MARCKS, MARCKSL1, BASP1, or a fragment of MARCKS, MARCKSL1, or BASP1. In some aspects, variants or variants of fragments of BASP1 share at least about 70%, at least about 80%, at least about 85%, at least about 90%, at least about 95%, at least about 96%, at least about 97%, at least about 98%, or at least about 99% sequence identity with BASP1 or with a functional fragment thereof. In some aspects, the variant or variant of a fragment of Scaffold Y protein retains the ability to be specifically anchored (or linked) to the luminal surface of EVs, e.g., exosomes. In some aspects, the Scaffold Y includes one or more mutations, e.g., conservative amino acid substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences is accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some aspects, Scaffold X is modified at any convenient location.

As used herein the term "producer cell" refers to a cell used for generating an EV. A producer cell can be a cell cultured in vitro, or a cell in vivo. A producer cell includes, but not limited to, a cell known to be effective in generating EVs, e.g., exosomes, e.g., HEK293 cells, Chinese hamster ovary (CHO) cells, mesenchymal stem cells (MSCs), BJ human foreskin fibroblast cells, s9f cells, fHDF fibroblast cells, AGE.HN® neuronal precursor cells, CAP® amniocyte cells, adipose mesenchymal stem cells, and RPTEC/TERT1 cells. In certain aspects, a producer cell is an antigen-presenting cell. In some aspects, the producer cell is a bacterial cell. In some aspects, a producer cell is a dendritic cell, a B cell, a mast cell, a macrophage, a neutrophil, a Kupffer-Browicz cell, or a cell derived from any of these cells, or any combination thereof. In some aspects, the producer cell is not a bacterial cell. In some aspects, the producer cell is not an antigen-presenting cell.

As used herein the term "associated with" refers to, e.g., a first moiety and a second moiety that are linked to each other by a covalent or non-covalent bond. The first moiety and the second moiety can be, e.g., a payload and an EV, a scaffold moiety and a payload, a scaffold moiety and an EV, or two payloads. In one aspect, the term "associated with" means a covalent, non-peptide bond or a non-covalent bond. For example, the amino acid cysteine comprises a thiol group that can form a disulfide bond or bridge with a thiol group on a second cysteine residue. Examples of covalent bonds include, but are not limited to, a peptide bond, a metal bond, a disulfide bond, a sigma bond, a pi bond, a double bond, a triple bond, a quadruple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

As used herein the term "linked to" or "conjugated to" are used interchangeably and refer to a covalent or non-covalent bond formed between a first moiety and a second moiety, e.g., (i) a payload, e.g., IL-12 and an EV, respectively, or (ii) a scaffold moiety expressed in or on the EV, e.g., Scaffold X (e.g., a PTGFRN protein), and a payload, e.g., 11-12, respectively, on the luminal surface of or on the external surface of the EV.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired EVs, that have undergone one or more processes of purification, e.g., a selection or an enrichment of the desired EV preparation. In some aspects, isolating or purifying as used herein is the process of removing, partially removing (e.g., a fraction) of the EVs from a sample containing producer cells. In some aspects, an isolated EV composition has no detectable undesired activity or, alternatively, the level or amount of the undesired activity is at or below an acceptable level or amount. In some aspects, an isolated EV composition has an amount and/or concentration of desired EVs at or above an acceptable amount and/or concentration. In some aspects, the isolated EV composition is enriched as compared to the starting material (e.g., producer cell preparations) from which the composition is obtained. This enrichment can be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In some aspects, isolated EV preparations are substantially free of residual biological products. In some aspects, the isolated EV preparations are 100% free, 99% free, 98% free, 97% free, 96% free, 95% free, 94% free, 93% free, 92% free, 91% free, or 90% free of any contaminating biological matter. Residual biological products can include abiotic materials (including chemicals) or unwanted nucleic acids, proteins, lipids, or metabolites. Substantially free of residual biological products can also mean that the EV composition contains no detectable producer cells and that only EVs are detectable.

As used herein, the term "ligand" refers to a molecule that binds to a receptor and modulates the receptor to produce a biological response. Modulation can be activation, deactivation, blocking, or damping of the biological response mediated by the receptor. Receptors can be modulated by either an endogenous or an exogenous ligand. Non-limiting examples of endogenous ligands include antibodies and peptides. Non-limiting examples of exogenous agonist include drugs, small molecules, and cyclic dinucleotides. The ligand can be a full, partial, or inverse ligand.

As used herein, the term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, $(scFv)_2$, Fab, Fab', and $F(ab')_2$, $F(ab1)_2$, Fv, dAb, and Fd fragments, diabodies, and antibody-related polypeptides. Antibody includes bispecific antibodies and multispecific antibodies so long as they exhibit the desired biological activity or function.

As used herein, the term "pharmaceutical composition" refers to one or more of the compounds described herein, such as, e.g., an EV mixed or intermingled with, or suspended in one or more other chemical components, such as pharmaceutically-acceptable carriers and excipients. One purpose of a pharmaceutical composition is to facilitate administration of preparations of EVs to a subject. The term "excipient" or "carrier" refers to an inert substance added to a pharmaceutical composition to further facilitate administration of a compound. The term "pharmaceutically-acceptable carrier" or "pharmaceutically-acceptable excipient" and grammatical variations thereof, encompasses any of the agents approved by a regulatory agency of the US Federal government or listed in the US Pharmacopeia for use in animals, including humans, as well as any carrier or diluent that does not cause the production of undesirable physiological effects to a degree that prohibits administration of the composition to a subject and does not abrogate the biological activity and properties of the administered compound. Included are excipients and carriers that are useful in preparing a pharmaceutical composition and are generally safe, non-toxic, and desirable.

As used herein, the term "payload" refers to a therapeutic agent that acts on a target (e.g., a target cell) that is contacted with the EV. Payloads that can be introduced into an EV and/or a producer cell include therapeutic agents such as, e.g., nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, and siRNA, antisense oligonucleotide, a phosphorodiamidate morpholino oligomer (PMO), or a peptide-conjugated phosphorodiamidate morpholino oligomer (PPMO)), amino acids (e.g., amino acids comprising a detectable moiety or a toxin or that disrupt translation), polypeptides (e.g., enzymes), lipids, carbohydrates, and small molecules (e.g., small molecule drugs and toxins).

As used herein, the term "substantially free" means that the sample comprising EVs comprise less than 10% of macromolecules by mass/volume (m/v) percentage concentration. In some aspects, some fractions contain less than 0.001%, less than 0.01%, less than 0.05%, less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 4%, less than 5%, less than 6%, less than 7%, less than 8%, less than 9%, or less than 10% (m/v) of macromolecules.

As used herein, the term "macromolecule" means nucleic acids, exogenous proteins, lipids, carbohydrates, metabolites, or a combination thereof.

As used herein, "sample" refers to a portion of a production volume taken from an EV-containing mixture. Samples can be derived from culture supernatant such as fed-batch culture supernatant or perfusion or continuous culture supernatant, or any mixture in which cellular growth and/or EV production occurs. The sample can be generated from culturing cells. Samples can also be derived from any steps of the downstream purification process.

Ranges recited herein are understood to be shorthand for all of the values within the range, inclusive of the recited endpoints. For example, a range of 1 to 10 is understood to include any number, combination of numbers, or sub-range from the group consisting of 1, 2, 3, 4, 5, 6, 7, 8, 9, and 10.

II. Methods of Quantifying Extracellular Vesicles

Extracellular vesicles are lipid bilayer vesicles that are enriched in cholesterol compared to the plasma membrane of the producer cell. The present disclosure therefore provides a method of measuring cholesterol in a sample to determine the concentration of extracellular vesicles in the sample. In some aspects, the disclosure is directed to a method of quantifying the concentration of extracellular vesicle in a sample, comprising analyzing a cholesterol content of the sample. In some aspects, the disclosure is directed a method of preparing a sample comprising one or more extracellular vesicles, the method comprising quantifying the concentration of extracellular vesicles in a sample by analyzing a cholesterol content of the sample. In some aspects, the cholesterol content can be used as a marker to calculate the concentration of EVs in a sample after comparison of the cholesterol content in a sample with a known concentration of extracellular vesicles as determined by another technique, such as, e.g., nanoparticle tracking analysis (NTA).

Traditional techniques to quantify extracellular vesicles include nanoparticle tracking analysis (NTA), which is a technique based on the ability to track the Brownian motion of particles in suspension. The basic data about the processed particles that can be acquired by this method include average size, modal value and size distribution. The typical NTA device is composed of a laser module, a microscope connected to a sensitive charge-coupled device (CCD) or complementary metal-oxide-semiconductor (CMOS) camera, a hydraulic pump and a measuring chamber. The hydraulic pump injects the extracellular vesicles into a measuring chamber at a fixed flow rate and exposes them to a narrow laser beam. Here, the movement of the illuminated particles over a certain time period is recorded by a highly sensitive camera installed onto an optical microscope, and the displacement of each particle is tracked and plotted as a function of time, which enables the calculation of particle size distribution by applying the two-dimensional Stokes-Einstein equation.

Using NTA alone is not amenable to high throughput analysis and indiscriminately analyzes non-EV particles found in cell culture supernatant, such as membrane fragments and protein aggregates, resulting in inaccurate measurements. NTA measurements are also dependent on operational parameters (e.g., laser intensity, camera level, etc.) and are subject to considerable operator-to-operator variability. There is a need for new techniques capable of measuring the extracellular vesicle particle count in a sample with high throughput and accuracy. The methods of the present disclosure are therefore directed to more effective methods of quantification of cholesterol levels in an extracellular vesicle sample wherein the cholesterol content can be used to calculate the extracellular vesicle particle count in a sample. The cholesterol concentration of a sample can be compared to a reference concentration curve, which can be generated by quantifying both the cholesterol content of a series of samples, and the extracellular vesicle concentrations of the same series of samples. In some aspects, the reference concentration curve is determined by more traditional, low-throughput techniques such as nanoparticle tracking analysis (NTA). Importantly, cholesterol levels can correlate linearly with the concentration of the EVs. Therefore, these reference concentration curves generated using a traditional extracellular quantification method can be used to calibrate the cholesterol quantification scale.

This calibration can be done by comparing the quantified cholesterol and extracellular vesicle concentrations of the reference concentration curve established with known extracellular vesicle concentrations, to the quantified cholesterol content of the unknown sample. After calibration is complete, this high-throughput cholesterol analysis technique can be used to rapidly and accurately calculate the concentration of extracellular vesicles in a sample via measurement of the cholesterol content. In some aspects, a reference concentration curve is established using samples with known concentrations of EVs as calculated by NTA. In some aspects, the reference EV concentration curve is used to calibrate a cholesterol concentration curve wherein the cholesterol content of a sample with a known concentration of EVs is measured. In some aspects, the calibrated cholesterol concentration curve can be used to determine the unknown concentration of EVs in a sample by quantifying the cholesterol content. In some aspects, the cholesterol content is correlated with the concentration of EVs in a sample. In some aspects, the cholesterol content is correlated linearly with the concentration of EVs in a sample. In some aspects, the disclosure is directed to measuring the cholesterol content of a sample comprising extracellular vesicles (e.g., exosomes). In some aspects, the present disclosure is directed to calculating the extracellular vesicle concentration in a sample by quantifying the cholesterol content in the sample and comparing it to a reference concentration curve generated by measuring the cholesterol count and extracellular vesicle concentration using a technique such as nanoparticle tracking analysis (NTA).

Other techniques that may be used include direct imaging, tunable resistive pule sensing (TRPS), dynamic light scattering, flow cytometry, and asymmetrical-flow field-flow fractionation. Direct imaging is a technique that allows for obtaining accurate size estimates of individual EVs with nanometer resolution. Alternatively, tunable resistive pule sensing (TRPS) is a technique that detects individual nanoparticles by measuring changes in electrical current as each particle passes through an adjustable nanopore. The magnitude of the recorded drop in electrical current (blockade event) can be accurately related to the volume of the passing particle. Flow cytometry may also be used to quantitate EVs in solution. However, EVs scatter 10-fold less light compared to polystyrene beads, which are typically used for calibration and as a result, most conventional flow cytometers are only able to detect single EVs above about 500 nm in size. Specifics regarding these techniques can be found, for example, in *Extracellular Vesicle Quantification and Characterization: Common Methods and Emerging Approaches*, Hartjes, T. A et al, Bioengineering 2019, 6, 7, which is incorporated by reference in its entirety.

In order to use cholesterol as a reliable measure of EV, e.g., exosome concentration in a sample, pre-treatment of the sample can be performed to remove non-EV cholesterol-containing species in the sample. For example, the sample may contain membrane fragments, apoptotic bodies, and other cholesterol-containing components that can interfere with and contaminate the extracellular vesicle cholesterol quantification. The methods of the present disclosure are therefore directed to preparing a sample comprising one or more EVs, e.g., exosomes, for analysis of a cholesterol content, comprising processing the sample using filtration, ultracentrifugation, or polyethylene glycol (PEG) precipitation. In some aspects, the sample is prepared prior to the cholesterol analysis.

Once EVs are isolated from other cholesterol-containing components, samples can then be analyzed for cholesterol using high-throughput methods, including plate-based fluorometric assays, with minimally processed samples to calculate EV concentration. One can use a commercially available kit such as the AMPLEX® Red Cholesterol Assay Kit and/or measured on bioprocess analyzers such as the CEDEX BIO HT™. The AMPLEX® Red Cholesterol Assay Kit provides a simple fluorometric method for the sensitive quantitation of cholesterol using a fluorescence microplate reader or fluorometer. Because a large portion of cholesterol in blood is in the form of cholesteryl esters, the assay is based on an enzyme-coupled reaction that detects both free cholesterol and cholesteryl esters. Cholesteryl esters are hydrolyzed by cholesterol esterase into cholesterol, which is then oxidized by cholesterol oxidase to yield $H_2O_2$ and the corresponding ketone product. The $H_2O_2$ is then detected using 10-acetyl-3,7-dihydroxyphenoxazine (AMPLEX® Red reagent), a highly sensitive and stable probe for $H_2O_2$. In the presence of horseradish peroxidase (HRP), AMPLEX® Red reagent reacts with $H_2O_2$ with a 1:1 stoichiometry to produce highly fluorescent resorufin. Because resorufin has absorption and fluorescence emission maxima of approximately 571 nm and 585 nm, respectively, there is little interference from autofluorescence in most biological samples.

Another method to quantify cholesterol content of extracellular vesicles is Raman spectroscopy. Raman spectroscopy can be used to generate "fingerprint" spectra to identify and quantify cholesterol and other components in a sample. Differences in peak intensities of reference cholesterol samples and extracellular vesicle samples can be used to calculate the amount of cholesterol in a sample. Extracellular vesicles can also be separated and analyzed using anion-exchange chromatography (AEX) techniques.

Other non-limiting, exemplary methods to quantify cholesterol content of extracellular vesicle species are liquid chromatography with Charged Aerosol Detection (CAD). In some aspects, cholesterol content can be measured by extracting lipids from EVs, e.g., exosomes, prior to injection into RP-HPLC with CAD and charged surface hybrid (CSH) C18 technology. Lipid (e.g., cholesterol) concentration can be quantified by comparing the area under the curve to a calibration curve using the ratio of the internal response factor.

III. Methods of Preparation and Purification of Extracellular Vesicles for Analysis Via Cholesterol Content The fundamentals of filtration are primarily dependent on size or molecular weight of the EVs. Therefore, based on their size, EVs can be isolated using membrane filters with defined molecular weight or size exclusion limits. This filtration process therefore separates extracellular vesicles such as exosomes from other components such as cell culture supernatants. In some aspects, filtration is used to isolate the cholesterol-containing EVs. In some aspects, one or more filtration steps are used to filter the EVs prior to analysis. In some aspects, the filter size is bigger than about 0.14 micron, about 0.16 micron, about 0.18 micron, about 0.2 micron, about 0.25 micron, about 0.3 micron, about 0.35 micron, about 0.4 micron, about 0.45 micron, about 0.5 micron, about 0.55 micron, about 0.6 micron, about 0.65 micron, or about 0.7 micron. In some aspects, the filter is smaller than about 0.25 micron, about 0.22 micron, about 0.2 micron, about 0.18 micron, about 0.16 micron, or about 0.14 micron. In some aspects, the filter is about 0.2 micron.

Filtration can also have to be performed at a flowrate commensurate to the total filter area to prevent any adsorption to the membrane filters. In some aspects, the filtration is performed at a flow rate of about 75 $L/m^2/h$ (Liters per square meter per hour), about 100 $L/m^2/h$, about 150 $L/m^2/h$, or about 200 $L/m^2/h$ of total filter area. In some aspects, the filtration is performed at a flow rate of about 25 $L/m^2/h$, about 50 $L/m^2/h$, about 300 $L/m^2/h$, about 500 $L/m^2/h$, or about 1000 $L/m^2/h$ of total filter area.

The filter type is also important to control the filtration and separation of the extracellular vesicles. The filters can be made of materials such as polyethersulfone, nylon, cellulose nitrate, or polytetrafluoroethylene (PTFE). In some aspects, the filter is a polyethersulfone (PES) membrane. The filtration process can be conducted in a sterile condition to prevent contamination with unwanted contaminants or microbes during the preparation of an extracellular vesicle sample for cholesterol analysis. In some aspects, the filtration process useful in the process is a sterile filtration. One or more sterile filtrations can be performed within the present methods. In some aspects, at least one, at least two, at least three, at least four, at least five, at least six, at least seven, at least eight, at least nine, at least ten, at least 11, at least 12, at least 13, at least 14, at least 15 at least 16, at least 17, at least 18, at least 19, at least 20, at least 25, at least 30, at least 35, at least 40, at least 45 or at least 50 filtrations can be introduced in the present methods. Another filtration approach that can be used is tangential flow filtration (TFF). Tangential flow filtration (TFF) is a rapid and efficient method for separation and purification of biomolecules. It can be applied to a wide range of biological fields such as immunology, protein chemistry, molecular biology, biochemistry, and microbiology. TFF can be used to concentrate and desalt sample solutions ranging in volume from 10 mL to thousands of liters, and can be used to fractionate large from small biomolecules, harvest cell suspensions, and clarify fermentation broths and cell lysates.

Ultracentrifugation is another technique that can be used to isolate EVs. Ultracentrifugation is a versatile and rigorous technique for characterizing the molecular mass, shape and interactions of biological molecules in solution. A current standard process for purification involves the use of density gradient ultracentrifugation processes, e.g., iodixanol, which relies on "floating" the lower density EVs through a gradient of decreasing density. In some aspects, the EVs can be isolated using an OPTIPREP™ Density Gradient Medium. Ultracentrifugation is a technique that uses very high rotational speeds to achieve separation for low-mass particles such as extracellular vesicles, e.g., exosomes. In some aspects, the EVs are prepared for cholesterol analysis using ultracentrifugation. Depending on the sample volume, a number of different ultracentrifugation speeds and times can be used to process the samples, such as those found in Table 1:

TABLE 1

| ROTOR TYPE | VOLUME | TIME | SPEED |
|---|---|---|---|
| TLA120.2 | 1 mL | 20 min | 100,000 × g |
| SW 32 Ti | 35 mL | 3 hours | 135,000 × g |
| Ti 45 | 100 mL | 1 hour | 135,000 × g |

Another ultracentrifugation approach to separate extracellular vesicles is a density gradient centrifugation using a component such as sucrose. Density gradient ultracentrifugation can be used to separate cells or particles based on their size and mass. Sucrose density gradient ultracentrifugation is a technique for fractionating macromolecules like DNA, RNA, and proteins. For this purpose, a sample containing a mixture of different size macromolecules is layered on the surface of a gradient whose density increases linearly from top to bottom. During centrifugation, different size macromolecules sediment through the gradient at different rates. The rate of sedimentation depends, in addition to centrifugal force, on the size, shape, and density of the macromolecules, as well as on the density and viscosity of the gradient. In this way, macromolecules are separated by size and larger macromolecules sediment towards the bottom of the gradient.

Polyethylene glycol (PEG) precipitation is another technique that can be used to prepare EVs for cholesterol analysis. Solutions of polyethylene glycol (PEG) can be used to precipitate and concentrate extracellular vesicles by causing a decrease in the solubility of compounds in the solutions of superhydrophilic polymers, PEGs. The procedure reduces to mixing of the sample and polymer solution, incubation, and sedimentation of EVs by low-speed centrifugation such as (1500×g). The EV pellet is then suspended in PBS for further analysis. The procedure is simple, fast, and scalable; does not deform EVs; and requires no additional equipment for isolation. In some aspects, a sample is prepared using polyethylene glycol (PEG) precipitation. In some aspects, a sample is prepared using PEG precipitation at a PEG concentration of about 5%, of about 6%, of about 7%, of about 8%, of about 9%, of about 10%, of about 11%, of about 12%, of about 13%, of about 14%, of about 15%, of about 16%, of about 17%, of about 18%, of about 19%, or of about 20%. In some aspects, a sample is prepared using PEG precipitation at a PEG concentration of about 10%. In some aspects, a sample is prepared using PEG precipitation at a PEG concentration of about 12%. In some aspects, a sample is prepared using PEG precipitation at a PEG concentration of about 15%.

The analysis techniques described herein are useful to quantify the cholesterol content of a sample. In some aspects, the concentration of cholesterol analyzed is less than about 50 ng/mL, less than about 60 ng/mL, less than about 70 ng/mL, less than about 80 ng/mL, less than about 90 ng/mL, less than about 100 ng/mL, less than about 110 ng/mL, less than about 120 ng/mL, less than about 130 ng/mL, less than about 140 ng/mL, less than about 150 ng/mL, less than about 160 ng/mL, less than about 170 ng/mL, less than about 180 ng/mL, less than about 190 ng/mL, less than about 200 ng/mL, less than about 250 ng/mL, less than about 300 ng/mL, less than about 350 ng/mL, less than about 400 ng/mL, less than about 450 ng/mL, or less than about 500 ng/mL.

In some aspects, the concentration of cholesterol analyzed is less than about 0.05 µg/mL, less than about 0.1 µg/mL, less than about 0.2 µg/mL, less than about 0.3 µg/mL, less than about 0.5 µg/mL, less than about 1 µg/mL, less than about 20 µg/mL, less than about 3 µg/mL, less than about 40 µg/mL, less than about 5 µg/mL, less than about 10 µg/mL, less than about 20 µg/mL, less than about 50 µg/mL, less than about 100 µg/mL, less than about 200 µg/mL, less than about 300 µg/mL, less than about 400 µg/mL, less than about 500 µg/mL, less than about 600 µg/mL, less than about 700 µg/mL, less than about 800 µg/mL, less than about 900 µg/mL, less than about 1000 µg/mL, less than about 1500 µg/mL, less than about 2000 µg/mL, less than about 2500 µg/mL, or less than about 3000 µg/mL. In some aspects, the concentration of cholesterol analyzed is less than about 100 µg/mL.

In some aspects, the concentration of cholesterol analyzed is less than about 10 µg/mL, less than about 9 µg/mL, less than about 8 µg/mL, less than about 7 µg/mL, less than about 6 µg/mL, less than about 5 µg/mL, less than about 4 µg/mL, less than about 3 µg/mL, less than about 2 µg/mL, or less than about 1 µg/mL. In some aspects, the concentration of cholesterol analyzed is less than about 1 µg/mL, less than about 0.9 µg/mL, less than about 0.8 µg/mL, less than about 0.7 µg/mL, less than about 0.6 µg/mL, less than about 0.5 µg/mL, less than about 0.4 µg/mL, less than about 0.3 µg/mL, less than about 0.2 µg/mL, or less than about 0.1 µg/mL. In some aspects, the concentration of cholesterol analyzed is less than about 10 mg/mL, less than about 9 mg/mL, less than about 8 mg/mL, less than about 7 mg/mL, less than about 6 mg/mL, less than about 5 mg/mL, less than about 4 mg/mL, less than about 3 mg/mL, less than about 2 mg/mL, or less than about 1 mg/mL.

In some aspects, the concentration of cholesterol analyzed is about 0.1 µg/mL, about 0.2 µg/mL, about 0.3 µg/mL, about 0.4 µg/mL, about 0.5 µg/mL, about 0.6 µg/mL, about 0.7 µg/mL, about 0.8 µg/mL, about 0.9 µg/mL, or about 1 µg/mL. In some aspects, the concentration of cholesterol analyzed is about 0.1 µg/mL, about 0.2 µg/mL, about 0.3 µg/mL, about 0.4 µg/mL, about 0.5 µg/mL, about 0.6 µg/mL, about 0.7 µg/mL, about 0.8 µg/mL, about 0.9 µg/mL, or about 1 µg/mL. In some aspects, the concentration of cholesterol analyzed is about 10 µg/mL, about 20 µg/mL, about 30 µg/mL, about 40 µg/mL, about 50 µg/mL, about 60 µg/mL, about 80 µg/mL, about 90 µg/mL, about 100 µg/mL, or about 1 µg/mL. In some aspects, the concentration of cholesterol analyzed is about 100 µg/mL to about 5000 µg/mL, e.g., about 100 µg/mL to about 200 µg/mL, about 200 µg/mL to about 300 µg/mL, about 300 µg/mL to about 400 µg/mL, about 400 µg/mL to about 500 µg/mL, about 500 µg/mL to about 600 µg/mL, about 600 µg/mL to about 700 µg/mL, about 800 µg/mL to about 900 µg/mL, about 900 µg/mL to about 1000 µg/mL, e.g., about 100 µg/mL, about 200 µg/mL, about 400 µg/mL, about 600 µg/mL, about 800 µg/mL, about 1000 µg/mL. In some aspects, the concentration of cholesterol analyzed is about 2000 µg/mL to about 3000 µg/mL, about 3000 µg/mL to about 4000 µg/mL, or about 4000 µg/mL to about 5000 µg/mL, e.g., about 2000 µg/mL, about 3000 µg/mL, about 4000 µg/mL, or about 5000 µg/mL.

The methods of the present disclosure use the measured cholesterol concentration as a marker for EV concentration. After comparison and correlation with a reference concentration curve via another method such as NTA, which has lower throughput, the cholesterol concentrations can be calibrated to the particle count measurements and therefore cholesterol content can be rapidly measured and used to determine the extracellular vesicle concentration in a sample. The methods of the present disclosure are therefore useful to calculate an EV concentration in the sample (EV/mL or in the case of exosomes, exo/mL). In some aspects, the concentration of exosomes in the analyzed sample is about $1\times10^{9}$ exo/mL to about $1\times10^{10}$ exo/mL, e.g., about $1\times10^{9}$ exo/mL, about $2\times10^{9}$ exo/mL, about $3\times10^{9}$ exo/mL, about $4\times10^{9}$ exo/mL, about $5\times10^{9}$ exo/mL, about $6\times10^{9}$ exo/mL, about $7\times10^{9}$ exo/mL, about $8\times10^{9}$ exo/mL, or about $9\times10^{9}$ exo/mL. In some aspects, the concentration of EVs in the analyzed sample is about $1\times10^{10}$ exo/mL to about $1\times10^{11}$ exo/mL, e.g., about $1\times10^{10}$ exo/mL, about $2\times10^{10}$ exo/mL, about $3\times10^{10}$ exo/mL, about $4\times10^{10}$ exo/mL, about $5\times10^{10}$ exo/mL, about $6\times10^{10}$ exo/mL, about $7\times10^{10}$ exo/mL, about $8\times10^{10}$ exo/mL, or about $9\times10^{10}$ exo/mL. In some aspects, the concentration of EVs in the analyzed sample is about $1\times10^{11}$ exo/mL to about $1\times10^{12}$ exo/mL, e.g., about $1\times10^{11}$ exo/mL, about $2\times10^{11}$ exo/mL, about $3\times10^{11}$ exo/mL, about $4\times10^{11}$ exo/mL, about $5\times10^{11}$ exo/mL, about $6\times10^{11}$ exo/mL, about $7\times10^{11}$ exo/mL, about $8\times10^{11}$ exo/mL, or about $9\times10^{11}$ exo/mL. In some aspects, the concentration of EVs in the analyzed sample is about $1\times10^{12}$ exo/mL to about $1\times10^{13}$ exo/mL, e.g., about $1\times10^{12}$ exo/mL, about $2\times10^{12}$ exo/mL, about $3\times10^{12}$ exo/mL, about $4\times10^{12}$ exo/mL, about $5\times10^{12}$ exo/mL, about $6\times10^{12}$ exo/mL, about $7\times10^{12}$ exo/mL, about $8\times10^{12}$ exo/mL, about $9\times10^{12}$ exo/mL, or about $1\times10^{13}$ exo/mL.

IV. Producer Cells and Cell Culture

Samples comprising EVs useful for the present methods can be obtained from in vitro cell culture or a harvest or a supernatant of the cell culture. The methods of the present disclosure are useful to analyze the cholesterol content of supernatant in any cell culture regardless of cell type.

EVs, e.g., exosomes, can be produced from a cell grown in vitro or a body fluid of a subject. When EVs, e.g., exosomes, are produced from in vitro cell culture, various producer cells, e.g., HEK293 cells, can be used. Additional cell types that can be used for the production of EVs, e.g., exosomes, described herein include, without limitation, mesenchymal stem cells, T cells, B cells, dendritic cells, macrophages, and cancer cell lines. Further examples of producer cells are known and include, e.g., Chinese hamster ovary (CHO) cells, mesenchymal stem cells (MSCs), BJ human foreskin fibroblast cells, fHDF fibroblast cells, AGE.HN® neuronal precursor cells, CAP® amniocyte cells, adipose mesenchymal stem cells, HT1080 cells, C2C12 cells, SIM-A9 cells, and RPTEC/TERT1 cells. In certain aspects, a producer cell is a dendritic cell, macrophage, B cell, mast cell, neutrophil, Kupffer-Browicz cell, adipose cell, cell derived from any of these cells, or any combination thereof. In some aspects, the producer cell is a bacterial cell. In some aspects, the producer cell is a plant cell.

Frequent sampling and analysis of cell culture supernatant is required to evaluate the kinetics of EV production and adequately explore different strategies to enhance productivity. It is not feasible to stringently purify large sample sets via density gradient ultracentrifugation and it is similarly unfeasible to analyze large sample sets on low throughput methods, such as NTA. The use of minimal sample processing such as filtration, coupled with high-throughput analysis of cholesterol content, offers a method to accurately quantify EV concentration in samples and therefore enables high-throughput screening for selection of high productivity cell clones, media optimization, bioreactor parameter optimization and evaluation of genetic engineering approaches for enhancing productivity.

In some aspects, EVs can be generated in a cell culture system and isolated from the producer cell. In some aspects, the sample comprising EVs can be obtained from a mammalian cell, a bacterial cell, a eukaryotic cell, a prokaryotic cell, a plant cell, an insect cell, or any combination thereof. In some aspects, the sample comprising EVs can be obtained from a mammalian cell. In some aspects, the sample comprising EVs can be obtained from a HEK293 cell culture. In some aspects, the sample comprising EVs can be a cell culture comprising cells producing EVs. The present disclosure provides a method for quantifying EVs which can be implemented on a large scale. In some aspects, the method can be applied to quantify EVs from a sample with a volume larger than about 1 L, about 5 L, about 10 L, about 15 L about 20 L, about 25 L, about 50 L, about 100 L, about 200 L, about 250 L, about 300 L, about 400 L, about 500 L, about 600 L, about 700 L, about 800 L, about 900 L, about 1000 L, or about 2000 L. In some aspects, the sample is obtained from a bioreactor with a large scale volume, e.g., 500 L, 1000 L, 1100 L, 1200 L, 1300 L, 1400 L, 1500 L, 1600 L, 1700 L, 1800 L, 1900 L, or 2000 L. In some aspects, the sample is obtained from a 2000 L bioreactor.

In some aspects, EVs can be generated from a perfusion cell culture. In some aspects, EVs can be generated from a batch cell culture. In some aspects, EVs can be generated from a fed-batch cell culture. In some aspects, the EVs can be generated from the cultures as described in WO02019/060629A1, the contents of which are expressly incorporated herein by reference. In some aspects, EVs can be generated from suspension or adherent cells. In some aspects, EVs can be generated from a HEK293 cell, a CHO cell, a BHK cell, a PERC6 cell, a Vero cell, a HeLa cell, a sf9 cell, a PC12 cell, a mesenchymal stem cell, a human donor cell, a stem cell, a dendritic cell, an antigen presenting cell, an induced pluripotent stem cell (IPC), a differentiated cell, a HT1080 cell, a C2C12 cells, a SIM-A9 cell, bacteria, *Streptomyces, Drosophila, Xenopus oocytes, Escherichia coli, Bacillus subtilis*, yeast, *S. cerevisiae, Picchia pastoris*, filamentous fungi, *Neurospora crassa*, and/or *Aspergillus nidulans*. In some aspects, the producer cell is a HEK293 cell. The process of EV generation would be generally applicable to bioreactor formats including AMBR, shake flasks, SUBS, Waves, Applikons, stirred tanks, CSTRs, adherent cell culture, hollow fibers, iCELLis, microcarriers, and other methods known to those of skill in the art.

The methods of the present disclosure are also directed to monitoring the extracellular vesicle content of the cell culture supernatant of a producer cell or cell culture at one or more time intervals to determine and monitor the extracellular vesicle production output. In some aspects, the cellular supernatant is collected and analyzed once per day. In some aspects, the cellular supernatant is collected and analyzed twice per day. In some aspects, the cellular supernatant is collected and analyzed three times per day.

The methods of the present disclosure are also useful for monitoring extracellular vesicle concentration over the entire length of an extracellular vesicle production run. Dynamic cell culture conditions in a bioreactor, or shake flask culture during a production run, results in changes of cell density and viable cell density, which in turn play a role in the quality and quantity of extracellular vesicle produced, and therefore requires consistent sampling and analysis to ensure that high quality extracellular vesicle production continues over the span of the production run. In some aspects, the cellular supernatant is collected and analyzed for a period of about 1 to about 90 days, about 1 to about 60 days, about 1 to about 45 days, about 1 to about 30 days, about 1 to about 15 days, or about 1 to about 3 days. In some aspects, the cellular supernatant is collected and analyzed for a period of about 1 to about 80 days. In some aspects, the cellular supernatant is collected and analyzed for a period of about 1 to about 70 days. In some aspects, the cellular supernatant is collected and analyzed for a period of about 1 to about 60 days. In some aspects, the cellular supernatant is collected and analyzed for a period of about 1 to about 50 days. In some aspects, the cellular supernatant is collected and analyzed for a period of about 1 to about 40 days. In some aspects, the cellular supernatant is collected and analyzed for a period of about 1 to about 30 days. In some aspects, the cellular supernatant is collected and analyzed for a period of about 1 to about 20 days. In some aspects, the cellular supernatant is collected and analyzed for a period of about 1 to about 10 days.

In some aspects, an exogenous sequence is transiently or stabled expressed in the producer cell or cell line via transfection, transformation, transduction, electroporation, or any other appropriate method of gene delivery or combination thereof known in the art. In some aspects, the exogenous sequence is integrated into the producer cell genome, or remains extra chromosomal. The exogenous sequence can be transformed as a plasmid. The exogenous sequences can be stably integrated into a genomic sequence of the producer cell, at a targeted site or in a random site. The exogenous sequences can be inserted into a genomic sequence of the producer cell, located within, upstream (5'-end) or downstream (3'-end) of an endogenous sequence encoding the EV, e.g., exosome, protein. Various methods known in the art can be used for the introduction of the exogenous sequences into the producer cell. For example, cells modified using various gene editing methods (e.g., methods using a homologous recombination, transposon-mediated system, loxP-Cre system, CRISPR/Cas9 CRISPR/Cfp1, CRISPR/C2c1, C2c2, or C2c3, CRISPR/CasY or CasX, TAL-effector nuclease or TALEN, or zinc finger nuclease (ZFN) systems) are within the scope of various aspects.

In some aspects, the producer cell is further modified to comprise an additional exogenous sequence. For example, an additional exogenous sequence can be included to modulate endogenous gene expression, modulate the immune response or immune signaling, or produce an EV, e.g., exosome, including a certain polypeptide as a payload or additional surface expressed ligand. In some aspects, the producer cell can be further modified to comprise an additional exogenous sequence conferring additional functionalities to EVs, e.g., exosomes, for example, specific targeting capabilities, delivery functions, enzymatic functions, increased or decreased half-life in vivo, etc. In some aspects, the producer cell is modified to comprise two exogenous sequences, one encoding the exosome protein or a modification or a fragment of the exosome protein, and the other encoding a protein conferring the additional functionalities to exosomes.

V. Extracellular Vesicle (e.g., Exosome) for the Analysis

As described supra, EVs, e.g., exosomes, described herein are EVs with a diameter between about 20-300 nm. In certain aspects, an EV, e.g., exosome, of the present disclosure has a diameter between about 20-290 nm, 20-280 nm, 20-270 nm, 20-260 nm, 20-250 nm, 20-240 nm, 20-230 nm, 20-220 nm, 20-210 nm, 20-200 nm, 20-190 nm, 20-180 nm, 20-170 nm, 20-160 nm, 20-150 nm, 20-140 nm, 20-130 nm, 20-120 nm, 20-110 nm, 20-100 nm, 20-90 nm, 20-80 nm, 20-70 nm, 20-60 nm, 20-50 nm, 20-40 nm, 20-30 nm, 30-300 nm, 30-290 nm, 30-280 nm, 30-270 nm, 30-260 nm, 30-250 nm, 30-240 nm, 30-230 nm, 30-220 nm, 30-210 nm, 30-200 nm, 30-190 nm, 30-180 nm, 30-170 nm, 30-160 nm, 30-150 nm, 30-140 nm, 30-130 nm, 30-120 nm, 30-110 nm, 30-100 nm, 30-90 nm, 30-80 nm, 30-70 nm, 30-60 nm, 30-50 nm, 30-40 nm, 40-300 nm, 40-290 nm, 40-280 nm, 40-270 nm, 40-260 nm, 40-250 nm, 40-240 nm, 40-230 nm, 40-220 nm, 40-210 nm, 40-200 nm, 40-190 nm, 40-180 nm, 40-170 nm, 40-160 nm, 40-150 nm, 40-140 nm, 40-130 nm, 40-120 nm, 40-110 nm, 40-100 nm, 40-90 nm, 40-80 nm, 40-70 nm, 40-60 nm, 40-50 nm, 50-300 nm, 50-290 nm, 50-280 nm, 50-270 nm, 50-260 nm, 50-250 nm, 50-240 nm, 50-230 nm, 50-220 nm, 50-210 nm, 50-200 nm, 50-190 nm, 50-180 nm, 50-170 nm, 50-160 nm, 50-150 nm, 50-140 nm, 50-130 nm, 50-120 nm, 50-110 nm, 50-100 nm, 50-90 nm, 50-80 nm, 50-70 nm, 50-60 nm, 60-300 nm, 60-290 nm, 60-280 nm, 60-270 nm, 60-260 nm, 60-250 nm, 60-240 nm, 60-230 nm, 60-220 nm, 60-210 nm, 60-200 nm, 60-190 nm, 60-180 nm, 60-170 nm, 60-160 nm, 60-150 nm, 60-140 nm, 60-130 nm, 60-120 nm, 60-110 nm, 60-100 nm, 60-90 nm, 60-80 nm, 60-70 nm, 70-300 nm, 70-290 nm, 70-280 nm, 70-270 nm, 70-260 nm, 70-250 nm, 70-240 nm, 70-230 nm, 70-220 nm, 70-210 nm, 70-200 nm, 70-190 nm, 70-180 nm, 70-170 nm, 70-160 nm, 70-150 nm, 70-140 nm, 70-130 nm, 70-120 nm, 70-110 nm, 70-100 nm, 70-90 nm, 70-80 nm, 80-300 nm, 80-290 nm, 80-280 nm, 80-270 nm, 80-260 nm, 80-250 nm, 80-240 nm, 80-230 nm, 80-220 nm, 80-210 nm, 80-200 nm, 80-190 nm, 80-180 nm, 80-170 nm, 80-160 nm, 80-150 nm, 80-140 nm, 80-130 nm, 80-120 nm, 80-110 nm, 80-100 nm, 80-90 nm, 90-300 nm, 90-290 nm, 90-280 nm, 90-270 nm, 90-260 nm, 90-250 nm, 90-240 nm, 90-230 nm, 90-220 nm, 90-210 nm, 90-200 nm, 90-190 nm, 90-180 nm, 90-170 nm, 90-160 nm, 90-150 nm, 90-140 nm, 90-130 nm, 90-120 nm, 90-110 nm, 90-100 nm, 100-300 nm, 110-290 nm, 120-280 nm, 130-270 nm, 140-260 nm, 150-250 nm, 160-240 nm, 170-230 nm, 180-220 nm, or 190-210 nm. The size of the EV, e.g., exosome, described herein can be measured according to methods described, infra.

In some aspects, an EV, e.g., exosome, of the present disclosure comprises a bi-lipid membrane ("EV, e.g., exosome, membrane"), comprising an interior surface and an exterior surface. In certain aspects, the interior surface faces the inner core (i.e., lumen) of the EV, e.g., exosome. In certain aspects, the exterior surface can be in contact with the endosome, the multivesicular bodies, or the membrane/cytoplasm of a producer cell or a target cell In some aspects, the EV, e.g., exosome, membrane comprises lipids and fatty acids. In some aspects, the EV, e.g., exosome, membrane comprises phospholipids, glycolipids, fatty acids, sphingolipids, phosphoglycerides, sterols, cholesterols, and/or phosphatidylserines.

In some aspects, the EV, e.g., exosome, membrane comprises an inner leaflet and an outer leaflet. The composition of the inner and outer leaflet can be determined by transbilayer distribution assays known in the art, see, e.g., Kuypers et al., Biohim Biophys Acta 1985 819:170. In some aspects, the composition of the outer leaflet is between approximately 70-90% choline phospholipids, between approximately 0-15% acidic phospholipids, and between approximately 5-30% phosphatidylethanolamine. In some aspects, the composition of the inner leaflet is between approximately 15-40% choline phospholipids, between approximately 10-50% acidic phospholipids, and between approximately 30-60% phosphatidylethanolamine.

In some aspects, EVs of the present disclosure comprise a membrane modified EV in its composition. For example, their membrane compositions can be modified by changing the protein, lipid, or glycan content of the membrane. Therefore, the present methods can be used to measure the concentration of membrane modified EVs.

More specifically, the EV, e.g., exosome, of the present can be produced from a cell transformed with a sequence encoding one or more additional exogenous proteins including, but not limited to ligands, cytokines, or antibodies, or any combination thereof. Exemplary additional exogenous proteins contemplated for use include the proteins, ligands, and other molecules described in detail in WIPO Publication WO 2019/133934, published Jul. 4, 2019, which is incorporated herein by reference in its entirety. Any of the one or more EV (e.g. exosome) proteins described herein can be expressed from a plasmid, an exogenous sequence inserted into the genome or other exogenous nucleic acid such as a synthetic messenger RNA (mRNA).

The methods of the present disclosure are also useful for quantifying the cholesterol content and calculating the extracellular vesicle concentration of extracellular vesicles that comprise surface modifications. In some aspects, the extracellular vesicle is surface-engineered. In some aspects, the surface-engineered EVs are generated by chemical and/or physical methods, such as PEG-induced fusion and/or ultrasonic fusion. In some aspects, the surface-engineered EVs, e.g., exosomes, are generated by genetic engineering. EVs produced from a genetically-modified producer cell or a progeny of the genetically-modified cell can contain modified membrane compositions. In some aspects, surface-engineered EVs, e.g., exosomes, have a scaffold moiety (e.g., exosome protein, e.g., Scaffold X) at a higher or lower density (e.g., higher number) or include a variant or a fragment of the scaffold moiety.

For example, surface-engineered EVs (e.g., Scaffold X-engineered EVs) can be produced from a cell (e.g., HEK293 cells) transformed with an exogenous sequence encoding a scaffold moiety (e.g., exosome proteins, e.g., Scaffold X) or a variant or a fragment thereof. EVs including scaffold moiety expressed from the exogenous sequence can include modified membrane compositions.

Various modifications or fragments of the scaffold moiety may be present on the extracellular vesicles subject to the analysis techniques of the present disclosure. For example, a scaffold moiety can be modified to have enhanced affinity to a binding agent and used for generating surface-engineered EVs that can be purified using the binding agent. Scaffold moieties modified to be more effectively targeted to EVs, e.g., exosomes, and/or membranes can be used. Scaffold moieties modified to comprise a minimal fragment required for specific and effective targeting to EVs, e.g., exosomes, membranes can be also used.

In some aspects, the EV, e.g., exosome, is genetically modified to comprise one or more exogenous sequences to produce modified EVs that express exogenous proteins on the vesicle surface. The exogenous sequences can comprise a sequence encoding the EV, e.g., exosome, protein or a modification or a fragment of the EV protein. An extra copy of the sequence encoding the EV, e.g., exosome, protein can be introduced to produce a surface-engineered EV having a higher density of the EV protein. An exogenous sequence encoding a modification or a fragment of the EV, e.g., exosome, protein can be introduced to produce a modified EV containing the modification or the fragment of the EV protein. An exogenous sequence encoding an affinity tag can be introduced to produce a modified EV, e.g., exosome, containing a fusion protein comprising the affinity tag attached to the EV protein. In some aspects, the exogenous sequence encodes for Scaffold X. Examples of Scaffold X can be found, for example, in WIPO Publication WO 2019/099942, published May 23, 2019, herein incorporated by reference in its entirety. In some aspects, the exogenous sequence encodes for Scaffold Y. Examples of Scaffold Y can be found, for example, in WIPO Publication WO 2019/040920, published Feb. 28, 2019, herein incorporated by reference in its entirety.

VI. Extracellular Vesicle Payloads

In some aspects, the EVs useful for the present methods are further modified with a payload, e.g., a ligand, a cytokine, an adjuvant, an immune modulator, an antigen, a vaccine, or any combination thereof. In some aspects, the payload comprises a small molecule, a peptide, a nucleotide, a protein, or any combination thereof. In some aspects, the payload comprises a therapeutic agent. In some aspects, the payload comprises a nucleotide, e.g., DNA, RNA, or any combination thereof, e.g., siRNA, shRNA, miRNA, antisense oligonucleotide, a phosphorodiamidate morpholino oligomer (PMO), or a peptide-conjugated phosphorodiamidate morpholino oligomer (PPMO). The payload can be associated with the exosome, e.g., via a Scaffold X or Scaffold Y as described herein.

or any combination thereof. In some aspects, the payload comprises a protein, e.g., a recombinant protein, a fusion protein, an antibody, or any combination thereof.

In some aspects, the payload comprises an immune modulator, e.g., an inhibitor for a negative checkpoint regulator or an inhibitor for a binding partner of a negative checkpoint regulator. In certain aspects, the negative checkpoint regulator comprises cytotoxic T-lymphocyte-associated protein 4 (CTLA-4), programmed cell death protein 1 (PD-1), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, or any combination thereof.

In some aspects, the payload comprises an activator for a positive co-stimulatory molecule or an activator for a binding partner of a positive co-stimulatory molecule. In certain aspects, the positive co-stimulatory molecule is a TNF receptor superfamily member (e.g., CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, AITR, TROY, CD358, TRAMP, and XEDAR). In some aspects, the activator for a positive co-stimulatory molecule is a TNF superfamily member (e.g., TNFα, TNF-C, OX40 L, CD40 L, FasL, LIGHT, TL1A, CD27 L, Siva, CD153, 4-1BB ligand, TRAIL, RANKL, TWEAK, APRIL, BAFF, CAMLG, NGF, BDNF, NT-3, NT-4, GITR ligand, and EDA-2). In further aspects, the positive co-stimulatory molecule is a CD28-superfamily co-stimulatory molecule (e.g., ICOS or CD28). In some aspects, the activator for a positive co-stimulatory molecule is ICOSL, CD80, or CD86.

In some aspects, the payload comprises a cytokine or a binding partner of a cytokine. In certain aspects, the cytokine comprises IL-2, IL-4, IL-7, IL-10, IL-12, IL-15, IL-21, or combinations thereof.

In some aspects, the payload comprises a protein that supports intracellular interactions required for germinal center responses. In certain aspects, the protein that supports intracellular interactions required for germinal center responses comprises a signaling lymphocyte activation molecule (SLAM) family member or a SLAM-associated protein (SAP). In some aspects, the SLAM family member comprises SLAM family member 1, CD48, CD229 (Ly9), Ly108, 2B4, CD84, NTB-A, CRACC, BLAME, CD2F-10, or combinations thereof.

In some aspects, the payload comprises an antigen, e.g., a tumor antigen, e.g., alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, TNF-related apoptosis-inducing ligand, Brachyury, (preferentially expressed antigen in melanoma (PRAME)), and any combination thereof.

In some aspects, the payload comprises an antigen derived from a bacterium, a virus, fungus, protozoa, or any combination thereof. In certain aspects, the payload comprises an antigen derived from an oncogenic virus. In some aspects, the payload comprises an antigen derived from a Human Gamma herpes virus 4 (Epstein Barr virus), influenza A virus, influenza B virus, cytomegalovirus, *Staphylococcus aureus, Mycobacterium tuberculosis, Chlamydia trachomatis*, HIV-1, HIV-2, corona viruses (e.g., MERS-CoV and SARS CoV), filoviruses (e.g., Marburg and Ebola), *Streptococcus pyogenes, Streptococcus pneumoniae*, Plasmodia species (e.g., *vivax* and *falciparum*), Chikungunya virus, Human Papilloma virus (HPV), Hepatitis B, Hepatitis C, human herpes virus 8, herpes simplex virus 2 (HSV2), *Klebsiella* sp., *Pseudomonas aeruginosa, Enterococcus* sp., *Proteus* sp., *Enterobacter* sp., *Actinobacter* sp., coagulase-negative staphylococci (CoNS), *Mycoplasma* sp., or combinations thereof.

In some aspects, the payload comprises an adjuvant, e.g., a Stimulator of Interferon Genes (STING) agonist, a toll-like receptor (TLR) agonist, an inflammatory mediator, or any combination thereof. In some aspects, an adjuvant is a STING agonist. In certain aspects, the STING agonist comprises a cyclic dinucleotide STING agonist or a non-cyclic dinucleotide STING agonist.

In some aspects, the payload comprises a TLR agonist. In certain aspects, the TLR agonist comprises a TLR2 agonist (e.g., lipoteichoic acid, atypical LPS, MALP-2 and MALP-404, OspA, porin, LcrV, lipomannan, GPI anchor, lysophosphatidylserine, lipophosphoglycan (LPG), glycophosphatidylinositol (GPI), zymosan, hsp60, gH/gL glycoprotein, hemagglutinin), a TLR3 agonist (e.g., double-stranded RNA, e.g., poly(I:C)), a TLR4 agonist (e.g., lipopolysaccharides (LPS), lipoteichoic acid, β-defensin 2, fibronectin EDA, HMGB1, snapin, tenascin C), a TLR5 agonist (e.g., flagellin), a TLR6 agonist, a TLR7/8 agonist (e.g., single-stranded RNA, CpG-A, Poly G10, Poly G3, Resiquimod), a TLR9 agonist (e.g., unmethylated CpG DNA), or any combination thereof.

In some aspects, the payload comprises a targeting moiety. In some aspects, the payload is an anti-clec9A antibody. In some aspects, the payload is an anti-CD3 antibody.

In some aspects, the payload linked to the EVs comprises two or more molecules, two, three, four, five, six, or seven molecules. In some aspects, the payload comprises IL-12, FLT3 L, CD40 L, or any combination thereof. In other aspects, an EV (e.g., exosome) comprises IL-12, CD40 L, and FLT3 L.

In some aspects, the immune modulator comprises Interleukin 12 (IL-12). Interleukin 12 (IL-12) is heterodimeric cytokine produced by dendritic cells, macrophages and neutrophils. It is encoded by the genes Interleukin-12 subunit alpha (IL12A) and Interleukin-12 subunit beta (IL12B), which encode a 35-kDa light chain (p35) and a 40-kDa heavy chain (p40), respectively. The active IL-12 heterodimer is sometimes referred to as p70. The p35 component has homology to single-chain cytokines, while p40 is homologous to the extracellular domains of members of the haematopoietic cytokine-receptor family. The IL-12 heterodimer therefore resembles a cytokine linked to a soluble receptor. IL-12 is involved in the differentiation of naive T cells into Th1 cells and sometimes known as T cell-stimulating factor. IL-12 enhances the cytotoxic activity of Natural Killer cells and CD8+ cytotoxic T lymphocytes. IL-12 also has anti-angiogenic activity, mediated by increased production of CXCL10 via interferon gamma. In some aspects, the EV, e.g., exosome, comprise IL-12.

In some aspects, the payload comprises a STING agonist. A STING agonist can comprise cyclic dinucleotides (CDNs) or non-cyclic dinucleotide agonists. Cyclic purine dinucleotides such as, but not limited to, cGMP, cyclic di-GMP (c-di-GMP), cAMP, cyclic di-AMP (c-di-AMP), cyclic-GMP-AMP (cGAMP), cyclic di-IMP (c-di-IMP), cyclic AMP-IMP (cAMP), and any analogue thereof, are known to stimulate or enhance an immune or inflammation response in a patient. In some aspects, the CDNs have 2'2', 2'3', 2'5', 3'3', or 3'5' bonds linking the cyclic dinucleotides, or any combination thereof. In some aspects, the extracellular vesicles to be quantified by the methods of the present disclosure comprise the STING agonist CL606, CL611, CL602, CL655, CL604, CL609, CL614, CL656, CL647, CL626, CL629, CL603, CL632, CL633, CL659, or a pharmaceutically acceptable salt thereof, which can be found along with additional STING agonist examples, in PCT Publication WO 2019/183571 A1, published Sep. 26, 2019, herein incorporated by reference in its entirety.

In some aspects, the EVs to be quantified by the methods of the present disclosure comprise an oligonucleotide. The oligonucleotides can be oligonucleotides of any kind, including antisense oligonucleotides. In some aspects, the antisense oligonucleotides are modified to additionally comprise one or more cholesterol molecules. In some aspects, the cholesterol is chemically conjugated to the 5' end of the antisense oligonucleotide. In some aspects, the cholesterol is chemically conjugated to the 3' end of the antisense oligonucleotide. In some aspects, a linker is placed between the cholesterol modification and the antisense oligonucleotide. In some aspects, the linker is tetraethylene glycol (TEG) and/or hexaethylene glycol (HEG). In some aspects, the EV, e.g., exosome, comprises an oligonucleotide. In some aspects, the EV, e.g., exosome, comprises an oligonucleotide targeting one or more genes, such as STAT3, STAT6, Nras, Kras, hNLR6, NLRP3, PMP22, or CEBP/β. Other Exemplary cancer gene targets include, but are not limited to Bax, Bc1-2, Focal adhesion kinase (FAK), Matrix metalloproteinase, VEGF, Fatty acid synthase, MDR, H-Ras, K-Ras, PLK-1, TGF-β, STAT3, STAT6, NLRP3, transthyretin, Huntingtin, CSF1R, EGFR, PKC-α, Epstein-Barr virus, HPV E6, BCR-Abl, and telomerase. The methods of the present disclosure can also involve the analysis of EV, e.g., exosome, carrying protein payloads. In some aspects, the EV, e.g., exosome, comprise a protein, an antibody, an antigen binding fragment thereof, or a fusion protein.

Other exemplary payloads can be found, for example, in WIPO Publication WO 2019/099942, published May 23, 2019, and WIPO Publication WO 2019/040920, published Feb. 28, 2019.

VII. Cell viability

Samples comprising EVs, e.g., exosomes, useful for the present methods can be obtained from in vitro cell culture or a harvest of a supernatant of the cell culture. Without wishing to be bound by theory, the viability of the producer cells can influence the characteristics of the EVs, e.g., exosomes. Cell viability assays are useful to determine optimal growth conditions of cell populations maintained in culture. Cell viability assays that can be used to assess proliferative activity, cell viability, metabolic activity, cell cycle phase, cell toxicity, and/or apoptosis are known in the art. The information derived from these assays can indicate whether a cell population that has been exposed to an experimental stimulus is healthy or dying, actively dividing or in stasis, or has committed to an apoptotic pathway.

The most direct means of measuring cell proliferation, a determination of the number of actively dividing cells, is to count the number of cells present. Cell viability, defined as the number of healthy cells in a sample, determines the amount of cells (regardless of phase around the cell cycle) that are living or dead, based on a total cell sample. While a basic cell count is a direct measure of proliferation and viability, measurements of DNA content or metabolic activity can also offer information about the physical condition and cell cycle stage.

In some aspects, the viability of the producer cells influences the cholesterol content of the EVs, e.g., exosomes. In some aspects, the viability of the producer cells influences the density and/or size of the EVs, e.g., exosomes. In some aspects, samples comprising EVs, e.g., exosomes, are produced from producer cells, e.g., HEK293 cells, with at least about 80% cell viability, at least about 85% cell viability, at least about 90% cell viability, at least about 95% cell viability, or about 100% cell viability. In some aspects, the samples comprising EVs, e.g., exosomes, are produced from producer cells with at least about 90% viability. In some aspects, the samples comprising EVs, e.g., exosomes, are produced from producer cells with at least about 80% viability.

EXAMPLES

Example 1

Separation of Cell Culture Supernatant

Figure 1B:
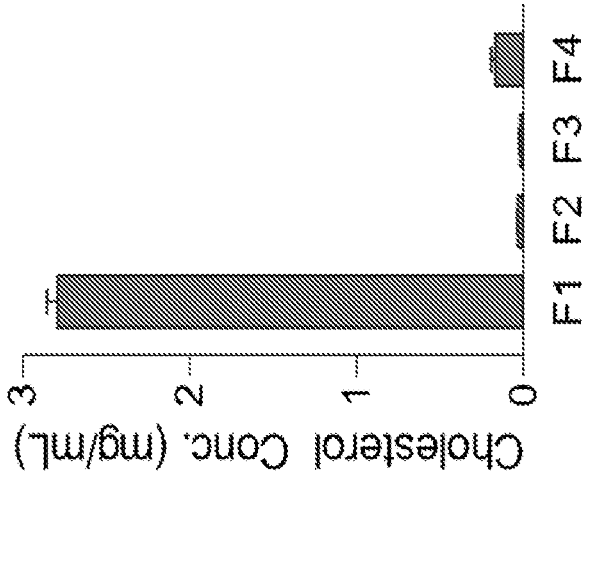
FIG. 1B shows analysis of four fractions using the AMPLEX® Red cholesterol assay showing enrichment of cholesterol in F1 only, which is the fraction containing exosomes.
Figure 1C:
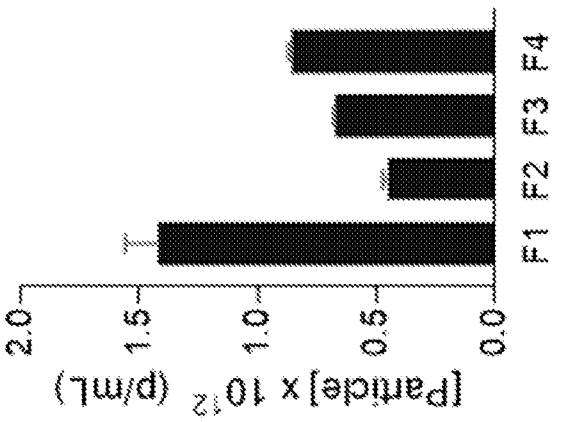
FIGS. 1C-1E show the total particle counts (FIG. 1C), protein concentration (FIG. 1D), and DNA concentration (FIG. 1E) for each of the four fractions.
Figure 1D:
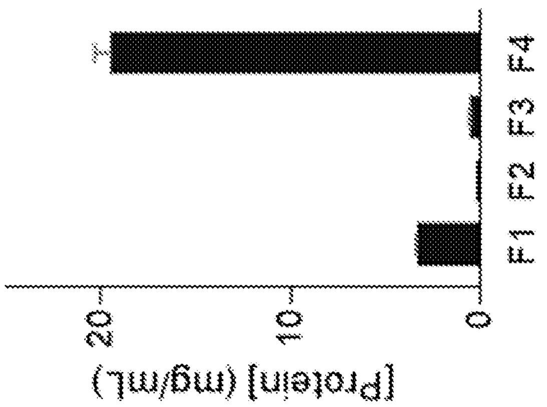
Figure 1E:
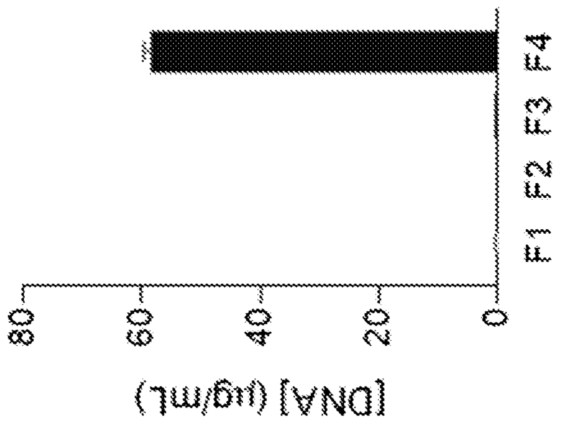
Figure 1F:
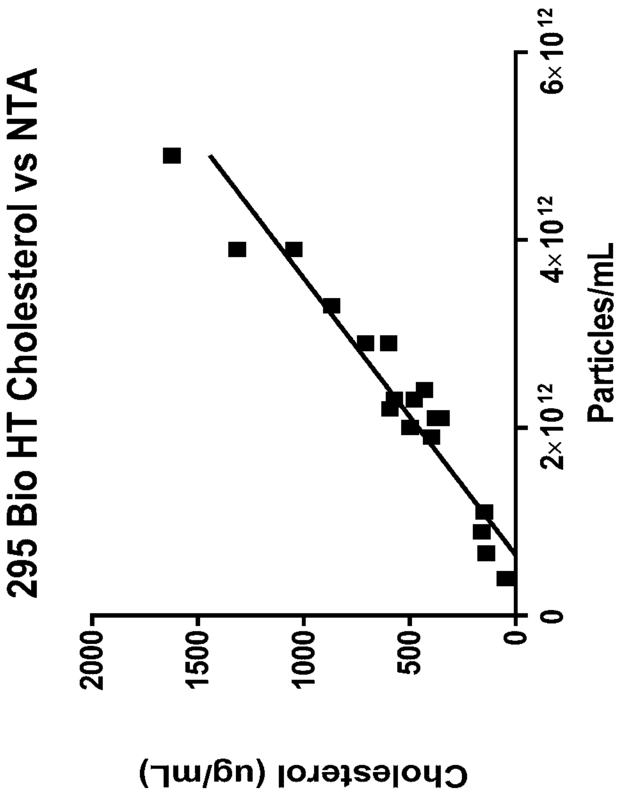
FIG. 1F shows characterization of 17 individual purified exosome samples by CEDEX™ Bio HT cholesterol assay and nanoparticle tracking analysis (NTA), showing a linear correlation.
Figure 1G:
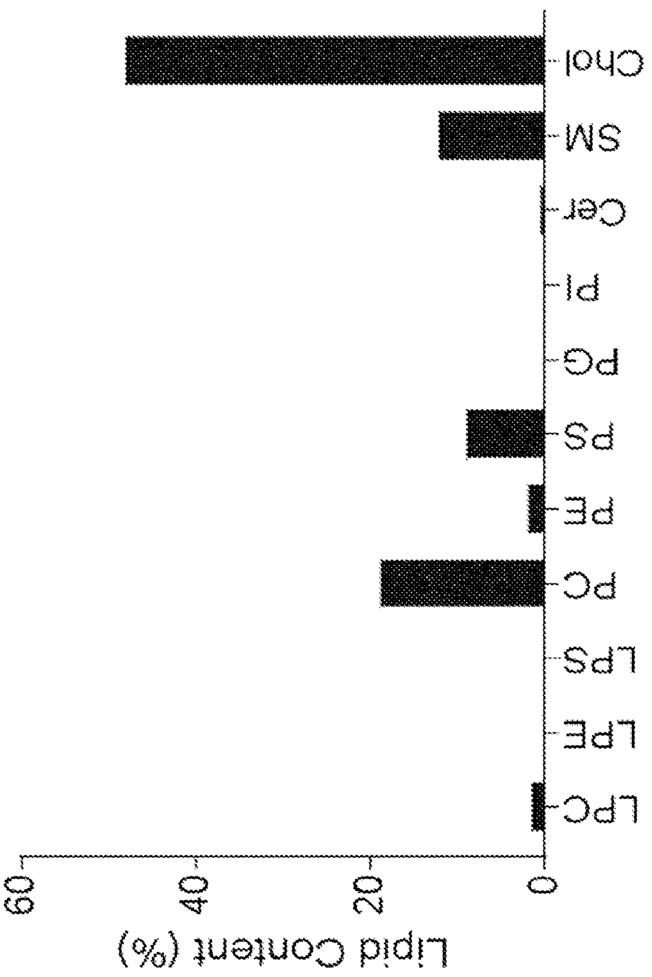
FIG. 1G shows the relative lipid content (percent) in the F1 fraction as measured using HPLC for each of the indicated lipids.

Exosomes in a sample were isolated according to the diagram in FIG. 1A. Cells were centrifuged at 6,000 g and filtered through a 0.45 μM PES filter. The sample was then subjected to nuclease treatment followed by additional centrifugation at 135,000 g, and resuspended. The F1 fraction, which contains the exosomes, was isolated, resuspended, and filtered using a 0.2 μM filter. Cholesterol quantification was performed on all four fractions F1-F4, and the results can be seen in FIG. 1B. The total particle counts (as measured using NTA; FIG. 1C), protein levels (as measured using BCA; FIG. 1D), and DNA concentrations (as measured using picogreen; FIG. 1E) were also analyzed for all four fractions. The lack of meaningful levels of cholesterol in F2-F4 enables accurate EV quantitation using crude ultracentrifuge material (e.g., input material for iodixanol gradient). Traditional NTA particle count analysis was also performed on the F1 fraction from 17 independent EV isolations to determine exosome particle count, and the results are shown in FIG. 1F. HPLC was used to analyze the lipid content of F1, and the relative levels of each of phosphatidylcholine, phosphatidylethanolamine, phosphatidylserine, phosphatidylglycerol, phosphatidylinositol, ceramide, sphingomyelin, cholesterol, and lyso-lipids are shown in FIG. 1G and Table 2.

TABLE 2

| | HEK Cell Pellets | | Exosomes from HEK | |
|---|---|---|---|---|
| Lipidomic Data | | % Total Lipid | | % Total Lipid |
| Cell densities (cells/ml) OR Particles/mL | 1.00E+07 | | 2.00E+13 | |
| Total Lipid (mg/mL) | 1.495 | | 5.088 | |
| Phospholipid (mg/mL) | 0.93087 | 62.27 | 1.9803 | 38.92 |
| Ceramide (mg/mL) | 0.01471 | 0.98 | 0.03287 | 0.65 |
| SM (mg/mL) | 0.08501 | 5.69 | 0.62485 | 12.28 |
| CHOL (mg/mL) | 0.4639 | 31.03 | 2.4504 | 48.16 |

These data indicate that cholesterol is present in both HEK cell membranes as well as exosomes. Concentration of cholesterol is enriched in exosomes, hence cholesterol concentration in a composition comprising exosomes can be measured and that cholesterol constitutes the major lipid component of these exosomes.

Cholesterol Quantification as Compared to NTA Particle Count

Figure 2A:
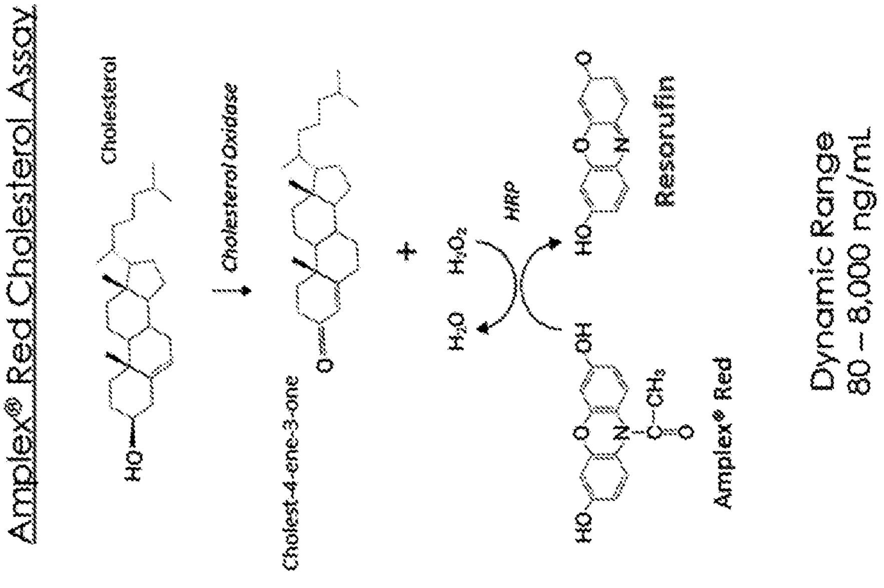
FIGS. 2A-2C show correlation of cholesterol measurement to iodixanol gradient prepared exosome particles. An AMPLEX® Red Cholesterol Assay (FIG. 2A) was used to measure cholesterol levels in EVs from 30 independent density gradient isolations (FIG. 2B). Three types of exosome particles are prepared by opti-gradients (exosomes expressing IL-12 on Scaffold X (e.g., PTGFRN) "Exo-IL12", native exosomes, and exosomes expressing Scaffold X (e.g., PTGFRN) alone) measured using the AMPLEX® Red cholesterol assay (FIG. 2C).
Figure 2B:
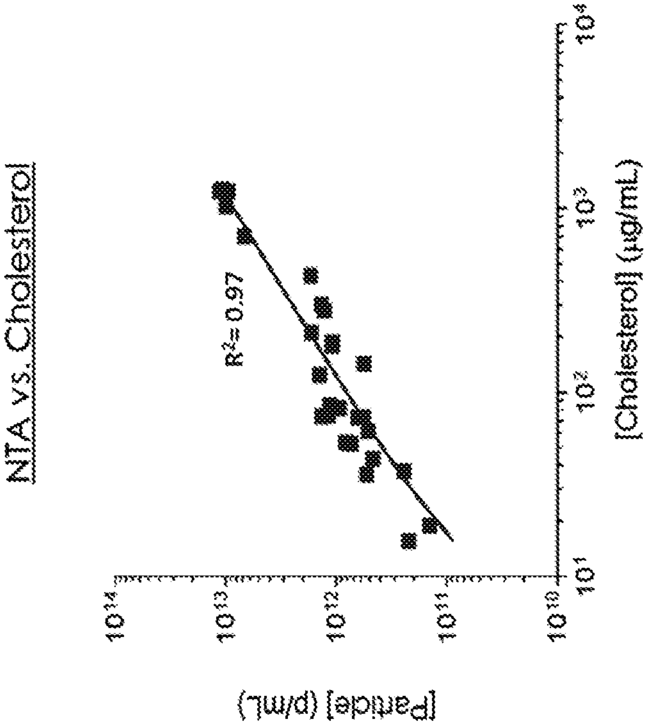
Figure 2C:
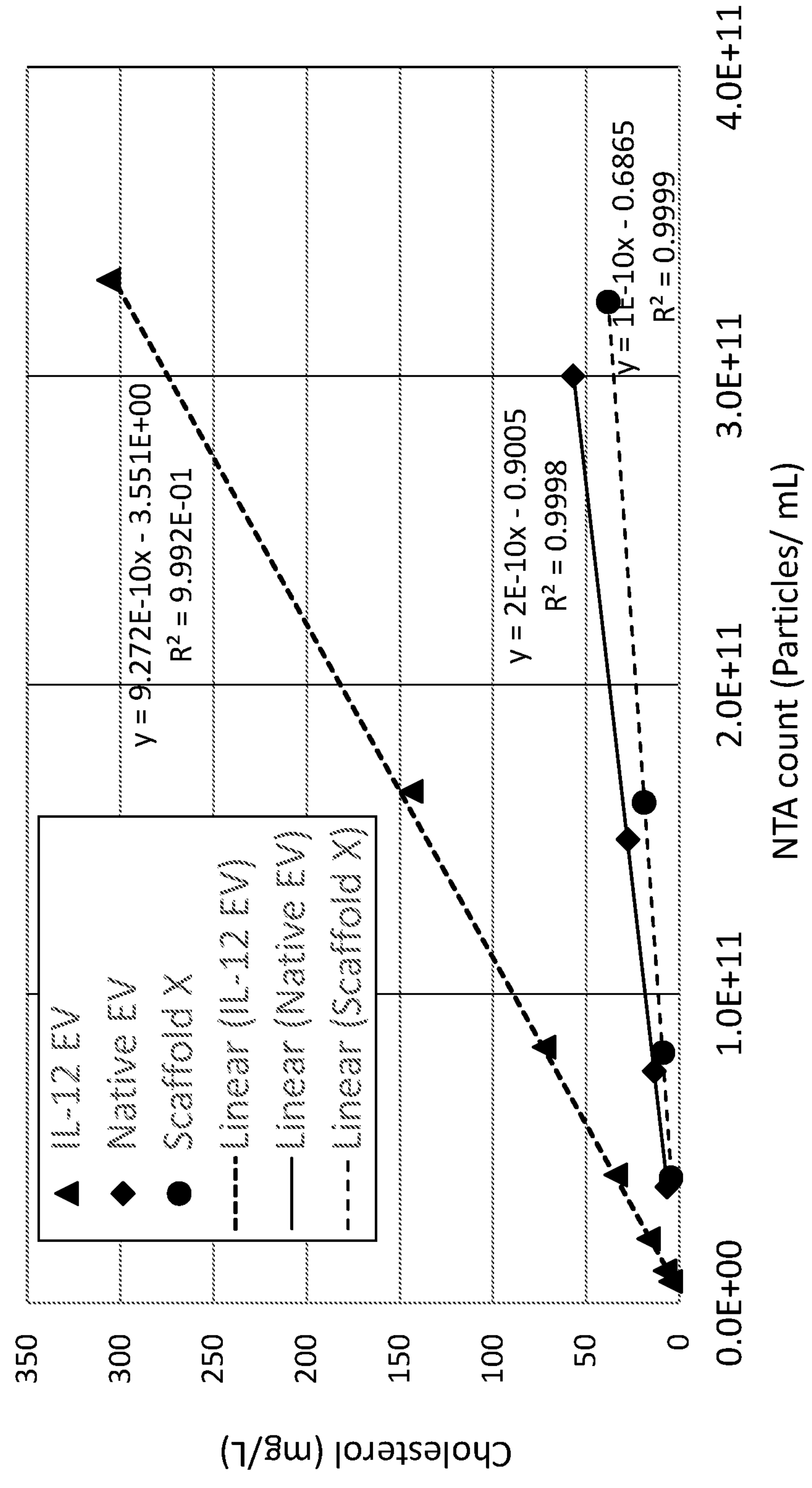

This correlation between NTA particle count and cholesterol concentration was further confirmed using a high throughput plate-based assay. Extracellular vesicles from about thirty independent density gradient isolations were characterized by measuring particle concentration (NTA) and cholesterol content (Amplex® Red), and NTA particle count was found to correlate with cholesterol concentration with an $R^2$ of 0.97 (FIGS. 2B-2C).

The correlation between NTA particle count and cholesterol concentration was measured between three different sample types: Native Exosomes, Exosomes expressing IL-12 (Exo-IL12) (e.g., exosomes engineered to display Prostaglandin F2 receptor negative regulator (PTGFRN) fused to IL-2), and exosomes expressing PTGFRN (e.g., exosomes engineered to display PTGFRN). EVs engineered to display PTGFRN or IL12 fused to PTGFRN were characterized by measuring particle concentration (NTA) and cholesterol content (AMPLEX® Red) and compared to wild type (WT) EVs. The linear regression between cholesterol concentration and NTA particle count can be seen in FIG. 2C for all three exosome types. Cholesterol content of Exo-IL12 was determined to be 8.16 μg/E11 particles. Cholesterol content for native exosomes was determined to be 1.82 μg/E11 particles. While the relationship is linear, the amount of cholesterol per particle varies between constructs. Nonetheless, these data show that engineered extracellular vesicles can be quantitated by measuring cholesterol.

Production Run Analysis Using a 3 L Perfusion Culture of HEK293 Cells

Figure 3A:
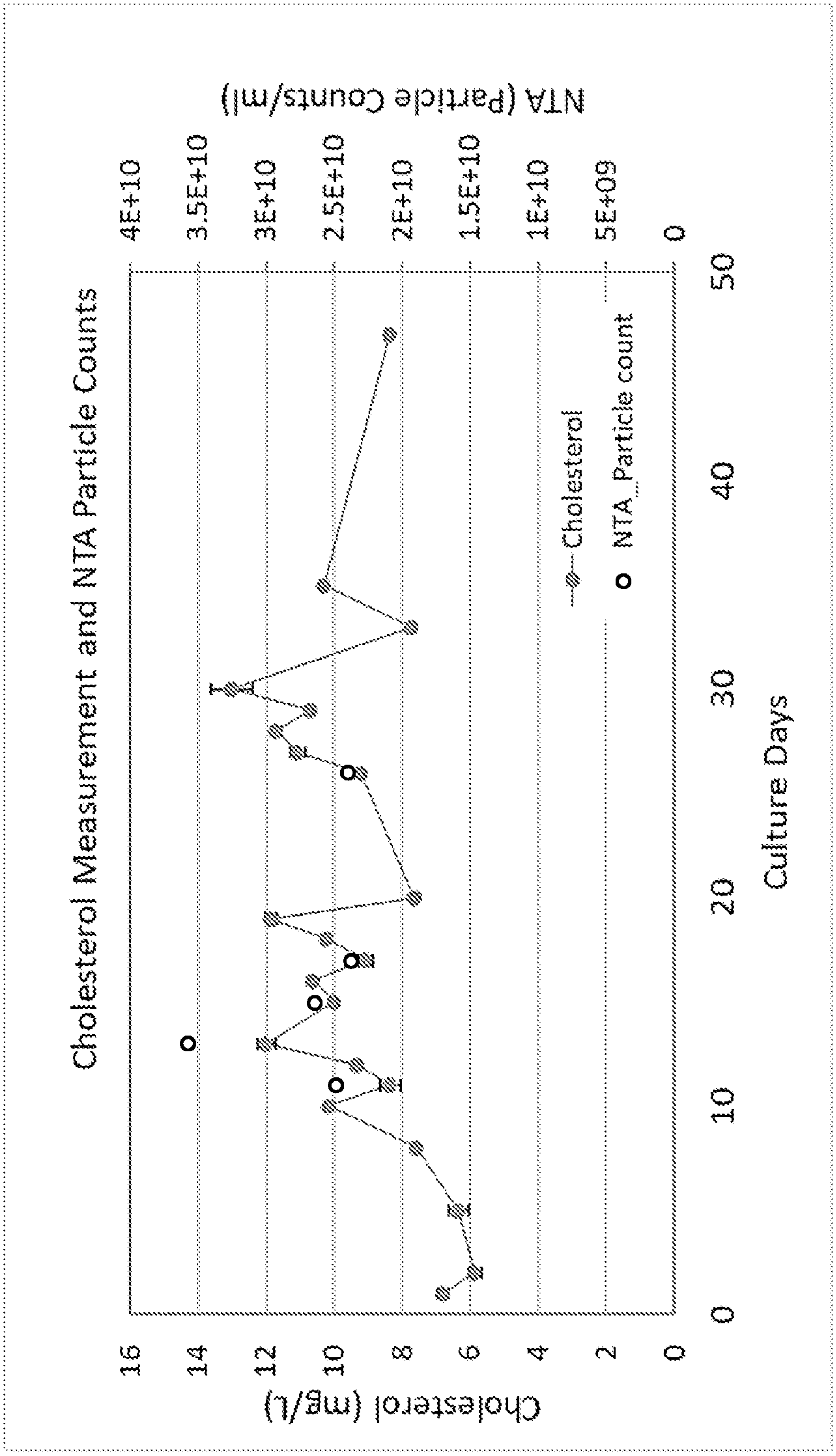
FIG. 3A shows cholesterol and NTA particle counts detected in bioreactor supernatant of a 3 L HEK-293 cells perfusion culture producing exosomes expressing IL-12 on Protein X ("Exo-IL12"). Cells were removed from bioreactor supernatant with 1600×g centrifugation for 5 min. Supernatant was filtered with 0.45 μm PES filters prior to cholesterol or NTA particle count measurement.
Figure 3C:
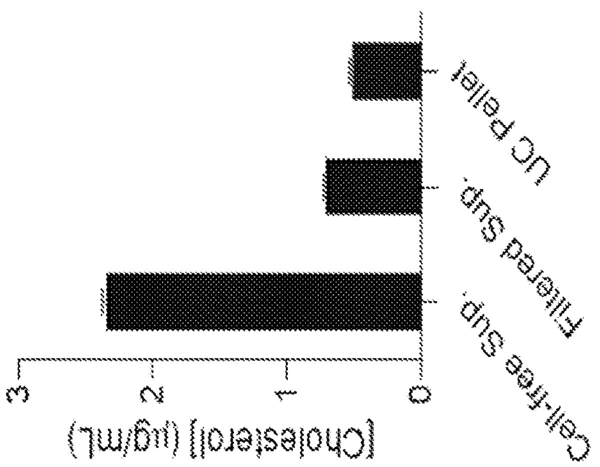
FIG. 3C shows the cholesterol concentration in cell-free cultured medium, filtered cultured medium, and crude UC pellet.
Figure 3B:
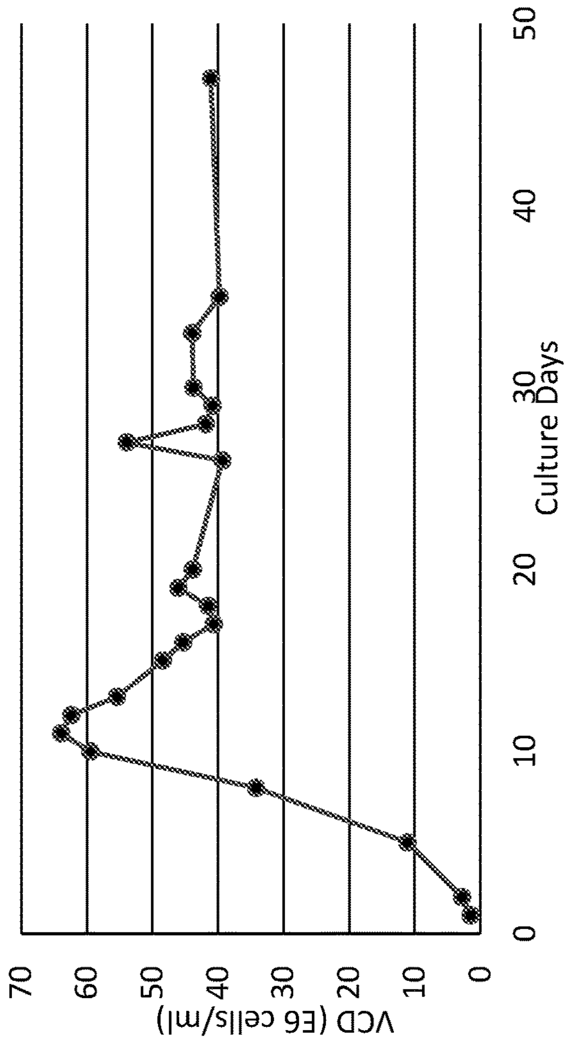
FIG. 3B shows viable cell density profiles for 3 L HEK-293 cells perfusion culture expressing Exo-IL12.
Figure 3D:
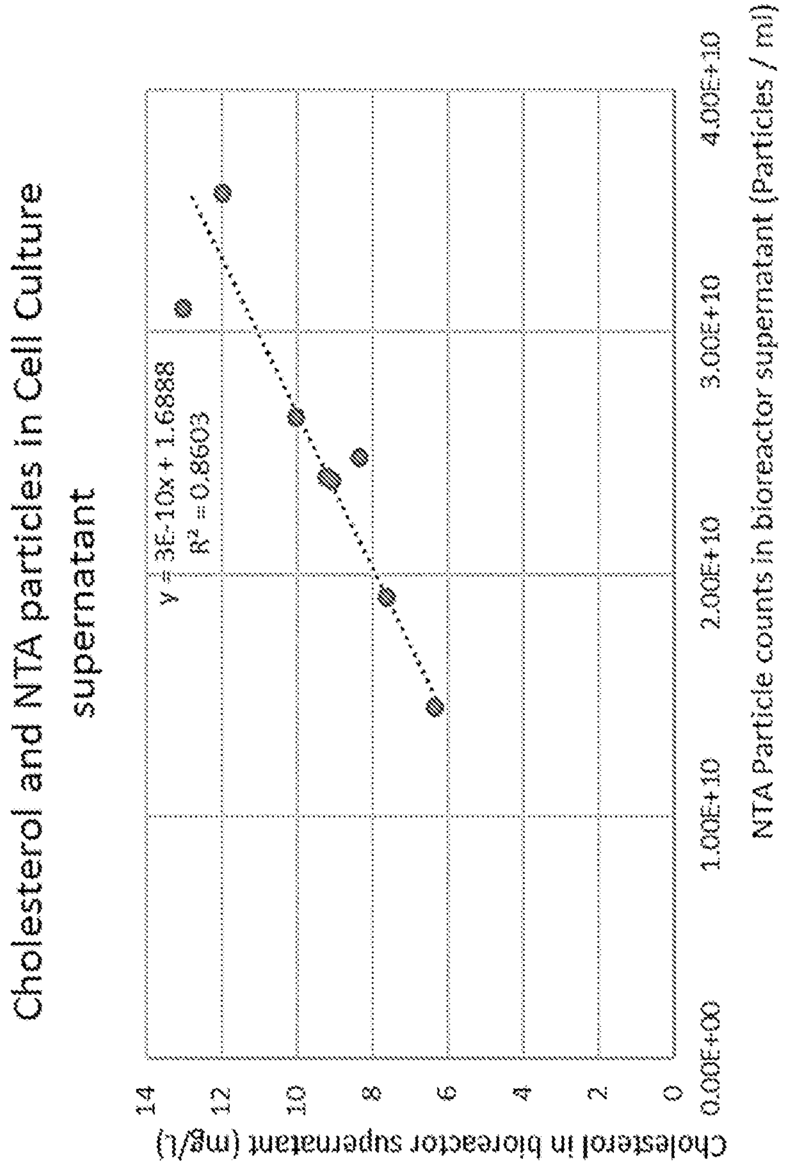
FIG. 3D shows a plot of cholesterol levels in a perfusion bioreactor and NTA particle counts in the bioreactor supernatant.

A production run of HEK293 cells in a 3 L perfusion culture reactor was performed. Bioreactor supernatant was collected after pelleting cells at 1600 g for 5 minutes, followed by filtration with a 0.45 μm PES filter. Approximately 75% of cholesterol measured in 0.45 μm filtered conditioned medium (Sup.) is recovered in crude UC pellet (FIG. 3C). Linear curves were generated to correlate cholesterol signal in these samples to NTA particle counts as measured (see FIG. 3A), and the calculated concentrations of cholesterol vs NTA particle count can be seen in FIG. 3D. Cell specific productivity of cholesterol production are calculated by normalizing the amounts of cholesterol detected in supernatant to the dilution rate from perfusion bioreactors and viable cell densities. The viable cell density (represented in $1\times10^6$ cells/mL) profile of the perfusion reactor run is shown in FIG. 3B. These data illustrate that monitoring cholesterol concentration of 0.45 μm filtered conditioned medium enables fast approximation of EV concentration throughout bioreactor production.

Exosomes from cell-free cultured medium after different clarification methods (0.45 μm filtration, crude UC pellet, PEG precipitation pellets, and OPTIPREP™ gradient F, 1 fraction) were analyzed and results are shown in Table 3.

TABLE 3

| | Cholesterol (μg/ml PRM) | % cholesterol recovered | Particles/mL | % particles recovered | Average Particle Size (nm) |
|---|---|---|---|---|---|
| Raw supernatant | 4.12 | 100.00% | 3.49E+11 | 100.00% | 274.63 |
| Raw supernatant after 0.45 μm filtration | 1.51 | 36.63% | 2.08E+11 | 59.60% | 221.67 |

TABLE 3-continued

| | Cholesterol (µg/ml PRM) | % cholesterol recovered | Particles/mL | % particles recovered | Average Particle Size (nm) |
|---|---|---|---|---|---|
| UC Pellet | 1.69 | 40.89% | 2.15E+11 | 61.60% | 216.33 |
| PEG precipitation Pellet | 1.97 | 47.78% | 8.59E+10 | 24.61% | 425.33 |
| Opti-gradients, F1 fraction | 0.60 | 14.48% | 2.40E+10 | 6.88% | 202.93% |

Figure 4A:
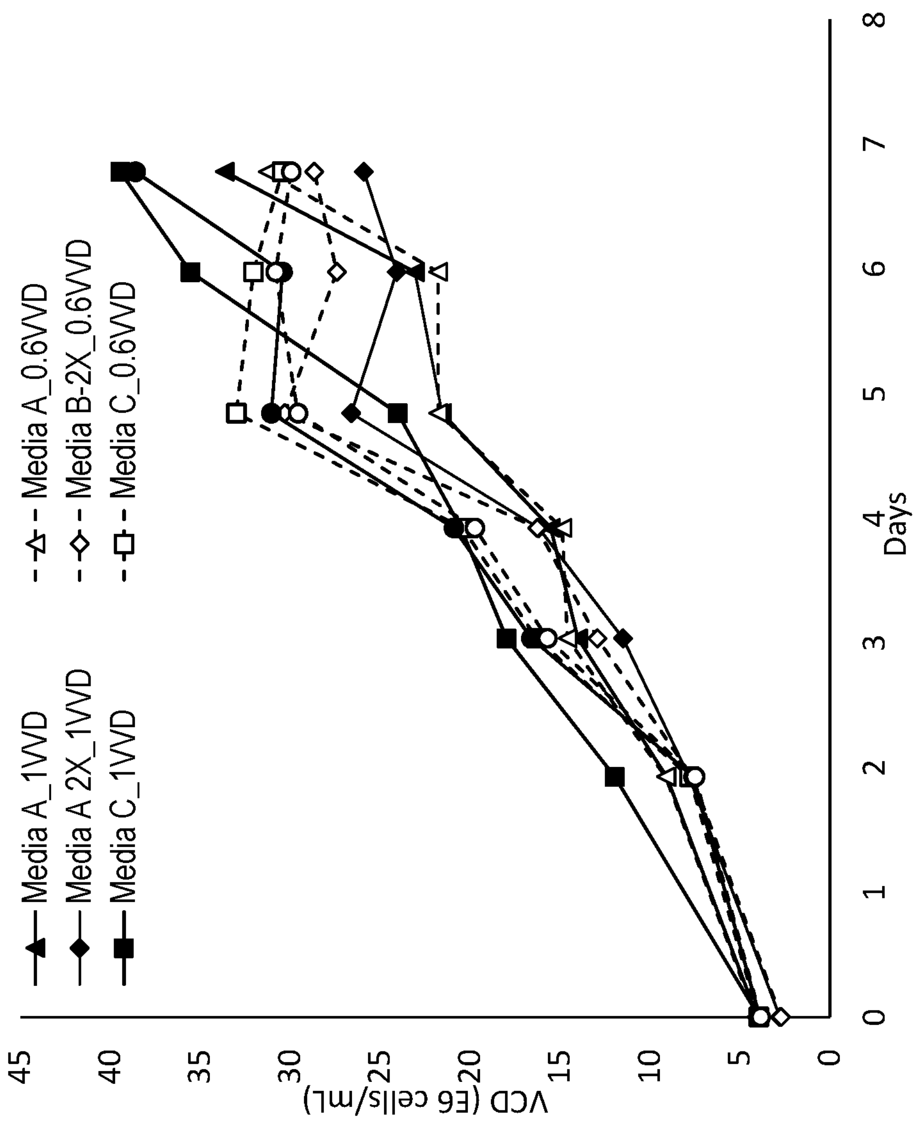
FIG. 4A shows viable cell density profiles of native HEK-293 cell lines grown in a 30 ml working volume shake flask. Batch re-feeds of 1 or 0.6 reactor volume per day (VVD) was performed daily from day 2 to day 6. Four types of perfusion media: Media A, Media A-2× concentrate, Media C with epidermal growth factor (EGF), and Media C without EGF were evaluated.
Figure 4B:
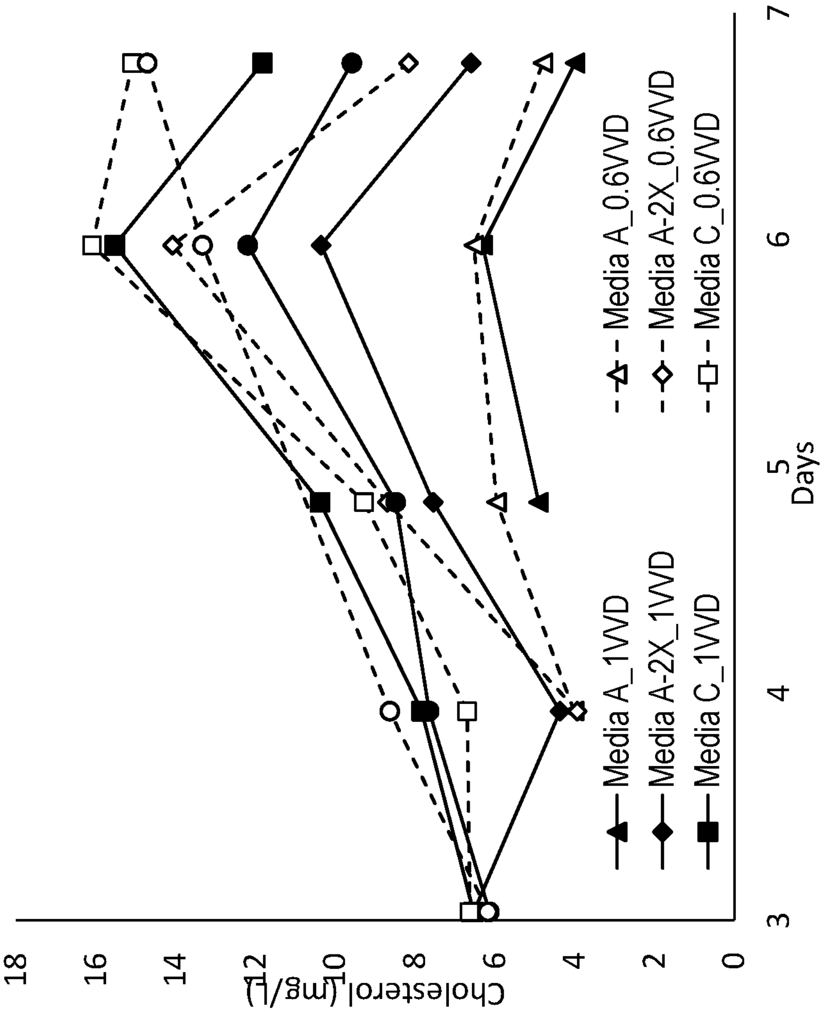
FIG. 4B shows levels of cholesterol present in the supernatant of the shake flask cultures measured daily from day 3.

Production Run Analysis Using a 30 mL Working Volume Shake Flask of HEK293 Cells Shake flasks were used to grow native HEK293 cells in a 30 mL working volume in a fed-batch approach. Batch refeeding was performed at a rate of one reactor volume per day (VVD) starting on day 2 of the culture until day 6. For separate types of perfusion media were tested, 1× permab, 2× permab, SAFC media with EGF, and SAFC media without EGF were evaluated at concentrations of 100% and diluted to 60%. The viable cell densities of each culture are shown in FIG. 4A across the media types for the duration of the culture. The cholesterol concentration was also calculated each day and is shown across the media types in FIG. 4B.

Example 2

Comparison of Cholesterol Quantification Methods

The AMPLEX® Red Cholesterol Assay and CEDEX™ BIO HT were used to quantify cholesterol in EV samples via enzymatic oxidation, with dynamic ranges of 80-8,000 g/mL and 4-800 µL/mL, respectively. Samples throughout various stages of purification were analyzed, from clarified cell culture medium to highly purified EVs separated on an iodixanol gradient. Several pre-processing methods were evaluated to remove non-EV cholesterol content prior to analysis. The AMPLEX® and CEDEX™ BIO HT assays were found to perform comparably for quantifying cholesterol in purified EVs ($R^2$=0.92). Importantly, cholesterol quantification on purified EV samples, ranging from $1e^{11}$ to $4e^{13}$ particles/mL, correlated well with NTA measurements ($R^2$=0.96). Either 45-04 filtration or an additional 16,000 RCF centrifugation step following clarification removed cholesterol associated with cellular debris or other non-EV sources.

Example 3

To track total mass balance of cholesterol throughout an entire production process, a sample construct will be harvested and purified from a 10 L shake flask production run. The sample will be centrifuged at 6,000 g and reconstituted in a 1 mL volume. The sample will then be treated with benzonase and reconstituted in a 1 mL volume. The sample will then be subjected to TFF and ultracentrifugation before being reconstituted in a volume of 50-100 µL. The sample will then be added to a gradient and reconstituted in a volume of 50 µL. The sample will then be subjected to ultracentrifugation at 20,000 g for 30 minutes. The pellet will then be suspended in 100-200 then filtered using a 0.45-04 filtration, and centrifuged for 3 hours. The pellet will then be retained for further analysis, including cholesterol levels and NTA counts.

Example 4

Figure 5B:
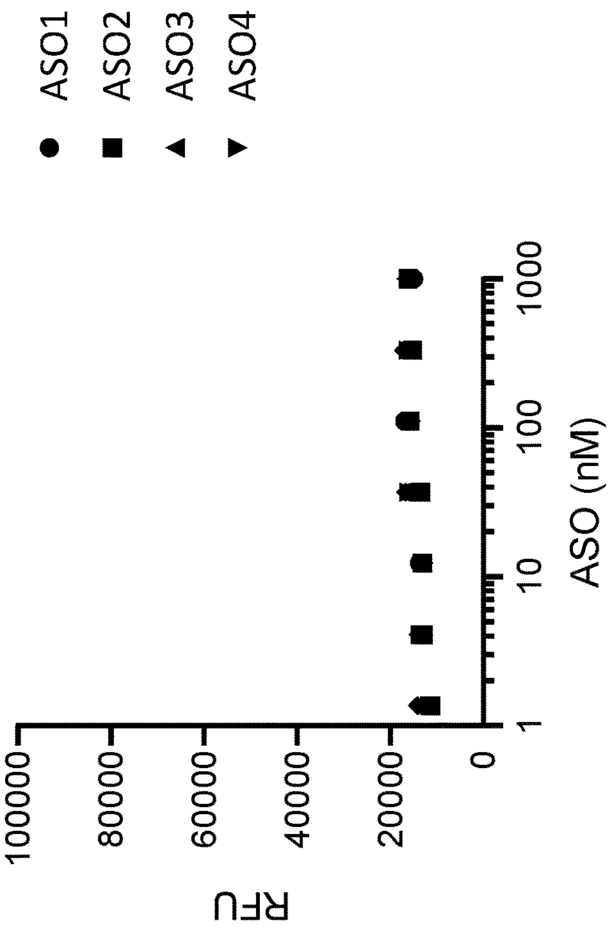
FIG. 5B shows cholesterol measurements for four different cholesterol conjugated antisense oligonucleotides (e.g., ASO1, ASO2, ASO3, and ASO4) using the AMPLEX® Red Cholesterol Assay and a BioTek Plate Reader. Cholesterol was not detected for any of the cholesterol conjugated antisense oligonucleotides.
Figure 5A:
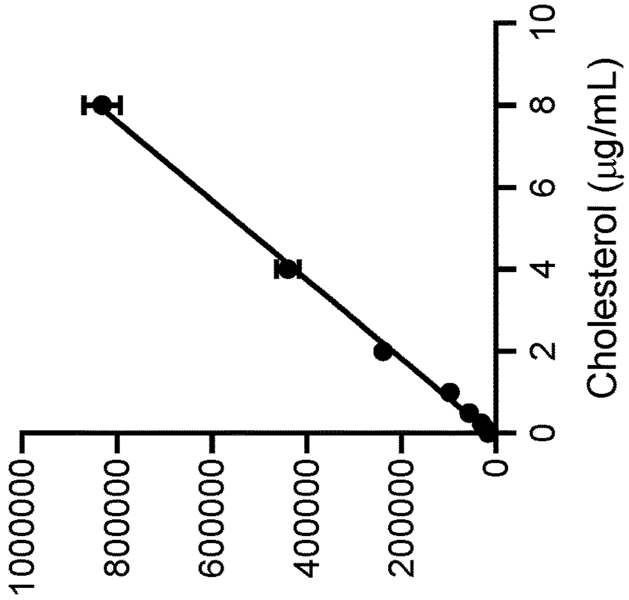
FIG. 5A shows a standard curve for cholesterol using AMPLEX® Red Cholesterol Assay and a BioTek Plate Reader.

To determine whether cholesterol conjugated antisense oligonucleotides (ASO) could interfere with the methods to determine EV concentration described herein, a cholesterol standard curve was prepared using a BioTek Plate Reader using the AMPLEX® Red Cholesterol assay (FIG. 5A). Cholesterol from four different cholesterol conjugated ASOs (e.g., ASO1, ASO2, ASO3, and ASO4) was measured using the AMPLEX® Red Cholesterol assay. Cholesterol was not detected in any of the cholesterol tagged ASOs tested (FIG. 5B), suggesting that loading cholesterol conjugated ASOs into EVs will not interfere with the methods for determining EV concentration described herein.

Example 5

Figure 6A:
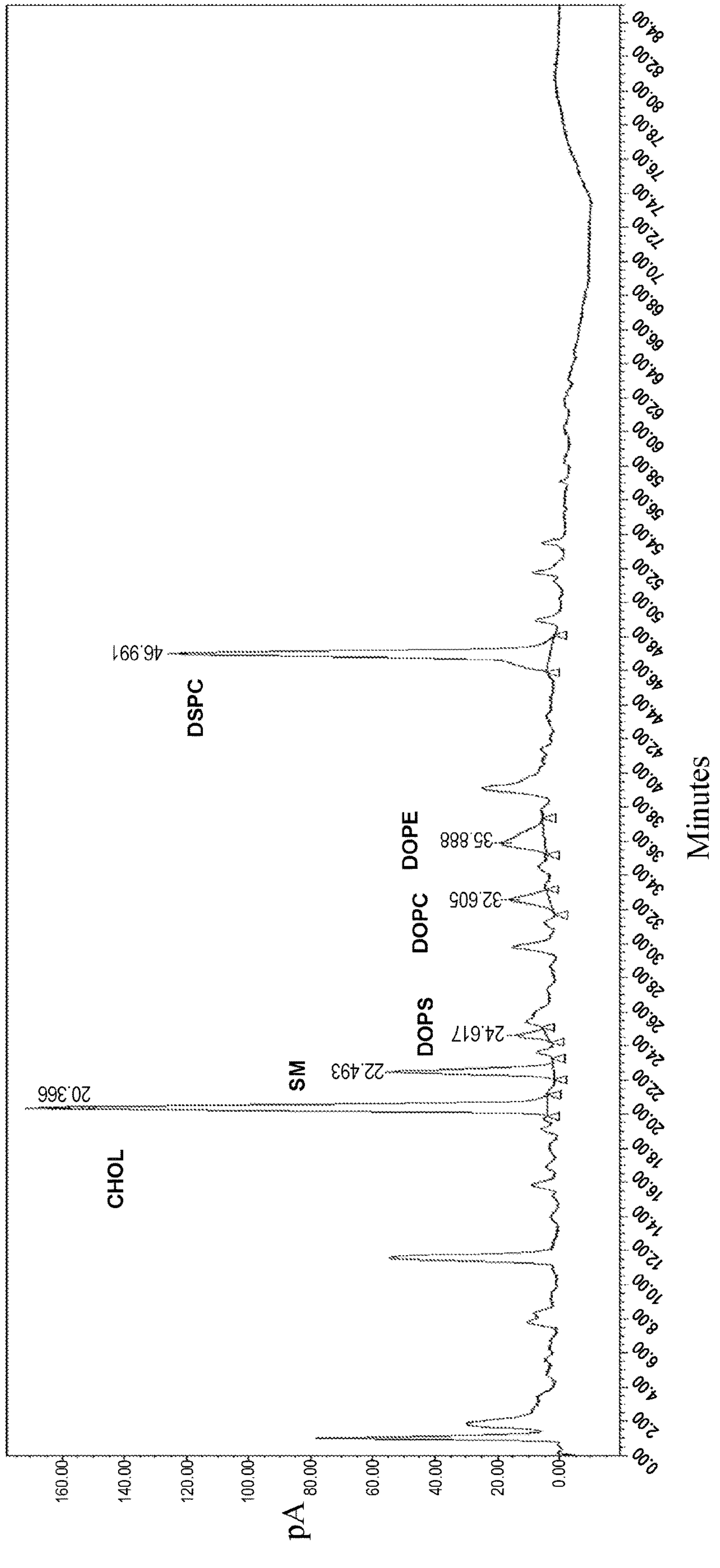
FIG. 6A shows a representative reversed-phase high performance liquid chromatography (RP-HPLC) chromatogram used to quantify cholesterol, sphingomyelin (SM), 1,2-Dioleoyl-sn-Glycero-3-phospho-L-serine (DOP S), 1,2-Dioleoyl-sn-Glycero Phosphocholine (DOPC), and 1,2-Dioleoyl-sn-Glycero-3-Phosphoethanolamine (DOPE) from purified exosomes expressing prostaglandin F2 receptor negative regulator (PTGFRN) using Charged Aerosol Detection (CAD) methods.
Figure 6B:
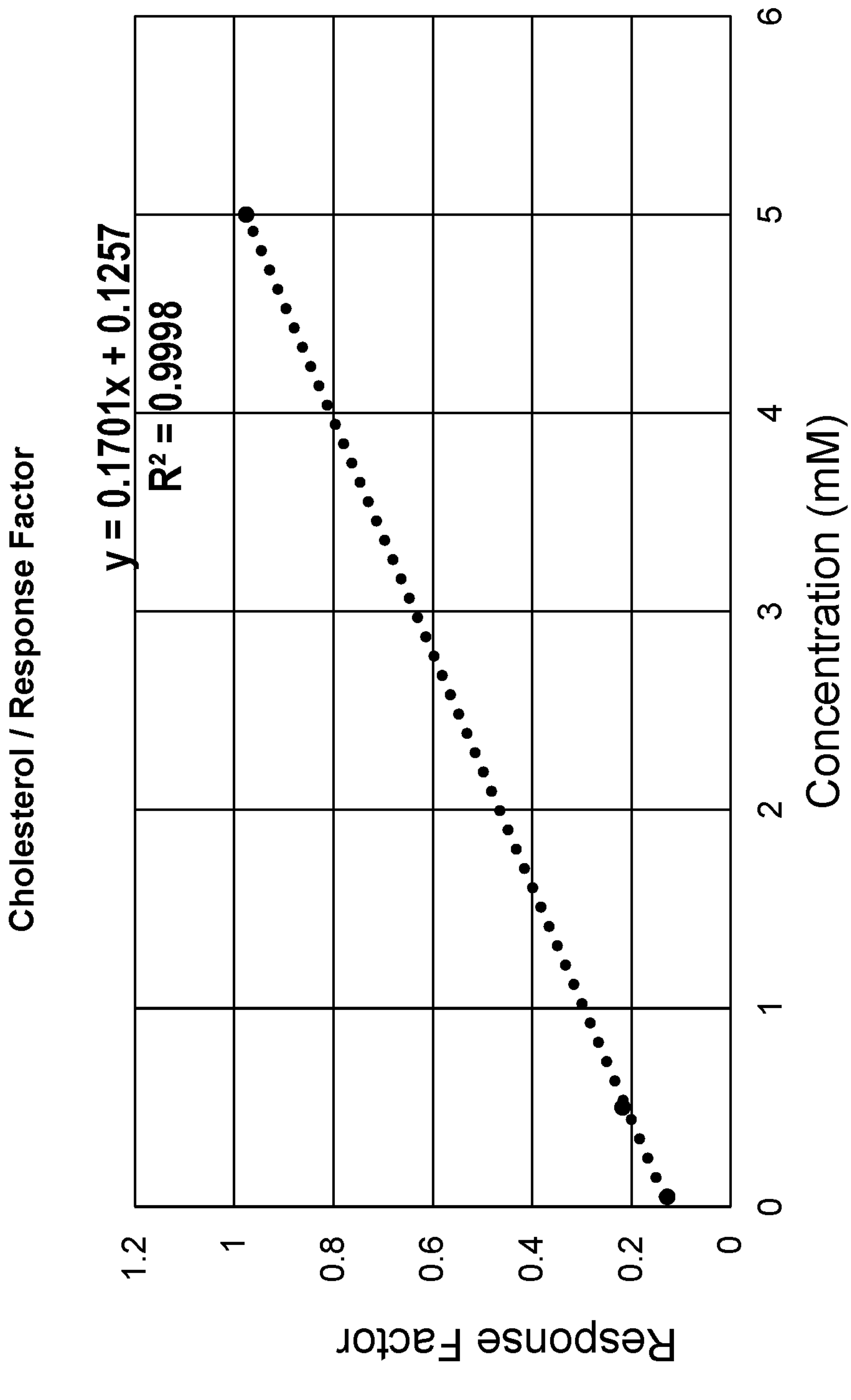
FIG. 6B shows the response factor (Y axis) as function of cholesterol concentration (x-axis) from cholesterol standards.

Charged Aerosol Detection (CAD) was used to quantify lipid concentrations from purified exosomes expressing PTGFRN produced at 250 L scale. Lipids were extracted from purified exosomes expressing PTGFRN using a Bligh and Dyer methanol-chloroform extraction method prior to injection into RP-HPLC with CAD and charged surface hybrid (CSH) C18 column technology. 50 µL of internal standard of DSPC was added to each sample before injection. Lipid concentration was quantified by comparing the area under the curve for each peak to a calibration curve for each of five lipids using the ratio of an internal response factor (FIG. 6A-6B). The calculated concentration of cholesterol, sphingomyelin (SM), 1,2-Dioleoyl-sn-Glycero-3-phospho-L-serine (DOPS), 1,2-Dioleoyl-sn-Glycero-3-Phosphocholine (DOPC), and 1,2-Dioleoyl-sn-Glycero-3-Phosphoethanolamine (DOPE) is shown in Table 4.

TABLE 4

| Name | Retention Time (min) | Calculated Concentration (µg/ml) |
|---|---|---|
| Cholesterol | 20.37 | 523.7 |
| SM | 22.49 | 214.4 |
| DOPS | 24.62 | 24.5 |
| DOPC | 32.61 | 9.2 |
| DOPE | 35.89 | 12.1 |
| DSPC | 7.0 | NA |
| Total | | 0.452245355 |

Calculations of lipid concentration were performed as follows: a calibration curve for each key lipid was obtained using the ratio of the internal response factor for each key standard lipid at various concentrations. The calibration curve equation was applied to all calculations to compensate for variability of the CAD response to each lipid. CAD response depends on interactions of specific lipids with the LC mobile phase and the formation efficiency of micro droplets of each lipid, which is affected by organic solvent content during nebulization. In order to successfully address the complexity of the lipid profile in EVs, e.g., exosomes, and CAD response, a known amount of an internal lipid standard, 1,2-Distearoyl-sn-Glycero-3-Phosphocholine (DSPC), was added to all standard and unknown samples. The internal response factor (IRF) was calculated by the ratio of peak area against the concentration as shown below:

$$\text{Internal Response Factor} = \frac{\text{Area of } DSPC \times \text{Concentration of Specific Lipid}}{\text{Area of Specific Lipid} \times \text{Concentration of } DSPC}$$

A calibration curve for each lipid was generated to demonstrate the linearity of response factor and lipid concentration. The equation from the curve was used to calculate the unknown concentration of specific lipid in an unknown sample following the equation below:

$$\text{Concentration of Specific Lipid} = \frac{\text{Area of Specific Lipid} \times \text{Concentration of } DSPC \times IRF}{\text{Area of } DSPC}$$

In calculations for an unknown concentration of a specific lipid, the equation of the linear curve as the value for IRF was used and solved for lipid concentration. The above equation was simplified using abbreviated terminologies shown below:

$C_L$=Concentration of specific lipid, $A_L$=Area of specific lipid, $A_{IS}$=Area of internal standard, DSPC $C_{IS}$=Concentration of internal standard, DSPC m=slope of linear regression line (obtained from calibration curve)

b=intercept of linear regression line (obtained from calibration curve)

The new equation to calculate the unknown concentration of a specific lipid in an unknown EV, e.g., exosome, sample is derived from the following equations:

$$(C_L)(A_{IS}) = (A_L)(C_{IS})(m.C_L + b)$$

$$\downarrow$$

$$(C_L)(A_{IS}) = (A_L)(C_{IS})(m.C_L) + (A_L)(C_{IS})(b)$$

$$\downarrow$$

$$[(C_L)(A_{IS} - (A_L)(C_{IS})(m)] = (A_L)(C_{IS})(b)$$

$$\downarrow$$

$$C_L = \frac{A_L C_{IS} b}{A_{IS} - (A_L C_{IS} m)}$$

Example 6

The cholesterol concentration in exosomes isolated from five different cell types was determined. Exosome samples were prepared by OPTIPREP™ density gradient. Lipids were extracted from samples using a modified Bligh and Dyer extraction. Lipids were dried and resuspended in 0.5 mL 50:50 chloroform:methanol for LC-MS analysis. A tertiary standard containing cholesterol was serially diluted to generate a calibration curve for quantitative analysis. The concentration of cholesterol in the exosomes from four different cell types is shown in Table 5.

TABLE 5

| Cell origin for exosomes | Cholesterol concentration (ng/ml) |
|---|---|
| HEK-293 | 1690 |
| MSC | 2040 |
| HT1080 | 680 |
| C2C12 | 120 |

The Table shows that exosomes produced by various cells types contain a sufficient concentration of cholesterol, thereby allowing the application of the present methods.

Example 7

Figure 7A:
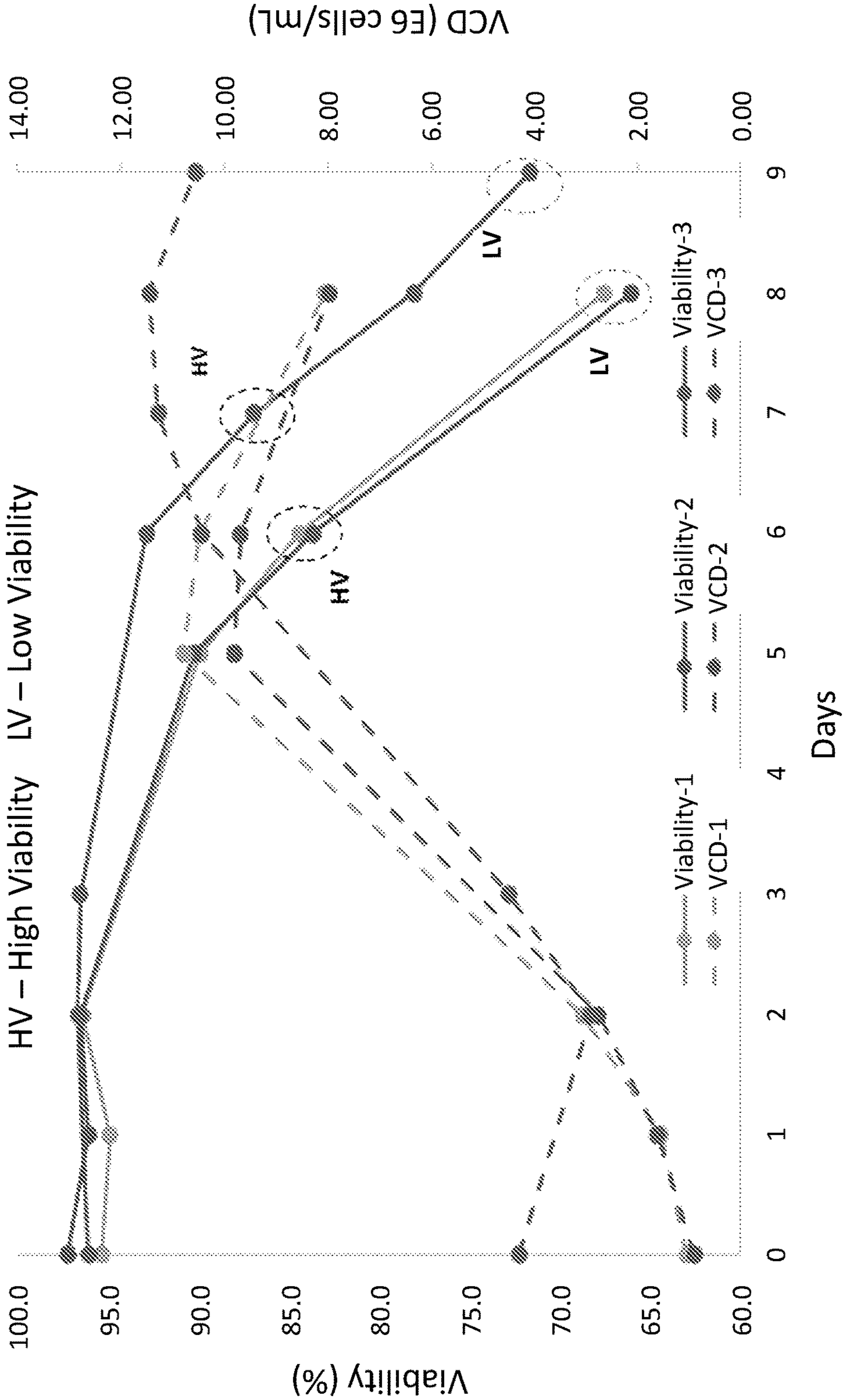
FIG. 7A shows the viability and viable cell density (VCD) of three groups of cells during a 9-day batch refeed experiment. The dotted circles show when samples were collected from the three groups.
Figure 7B:
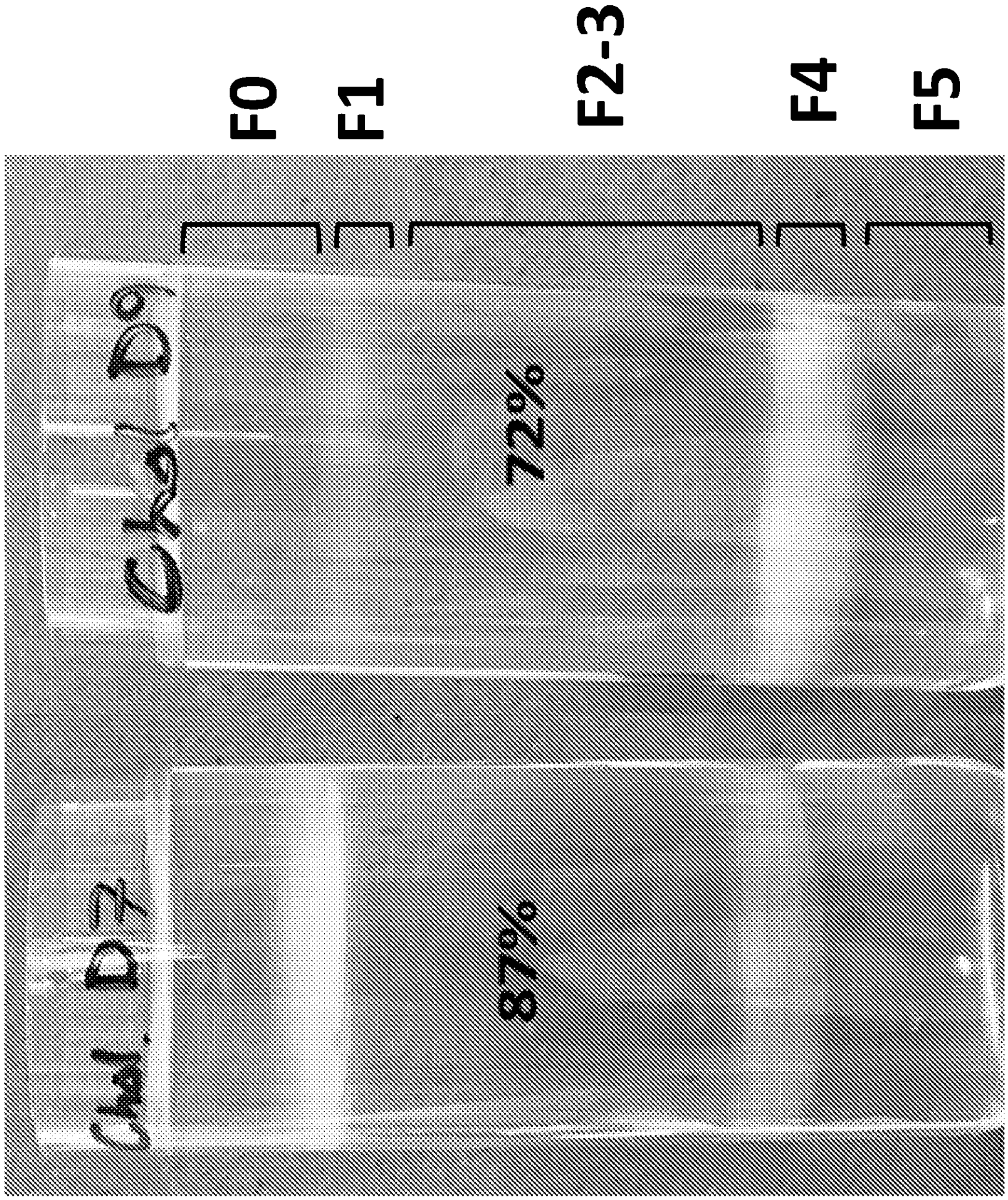
FIG. 7B shows representative OPTIPREP™ density gradient fractions from samples of cell-free culture medium taken when cell viability was high (higher than 80%, e.g., 87%) (FIG. 7B, left side) and when cell viability was low (65-72%) (FIG. 7B, right side).
Figure 7C:
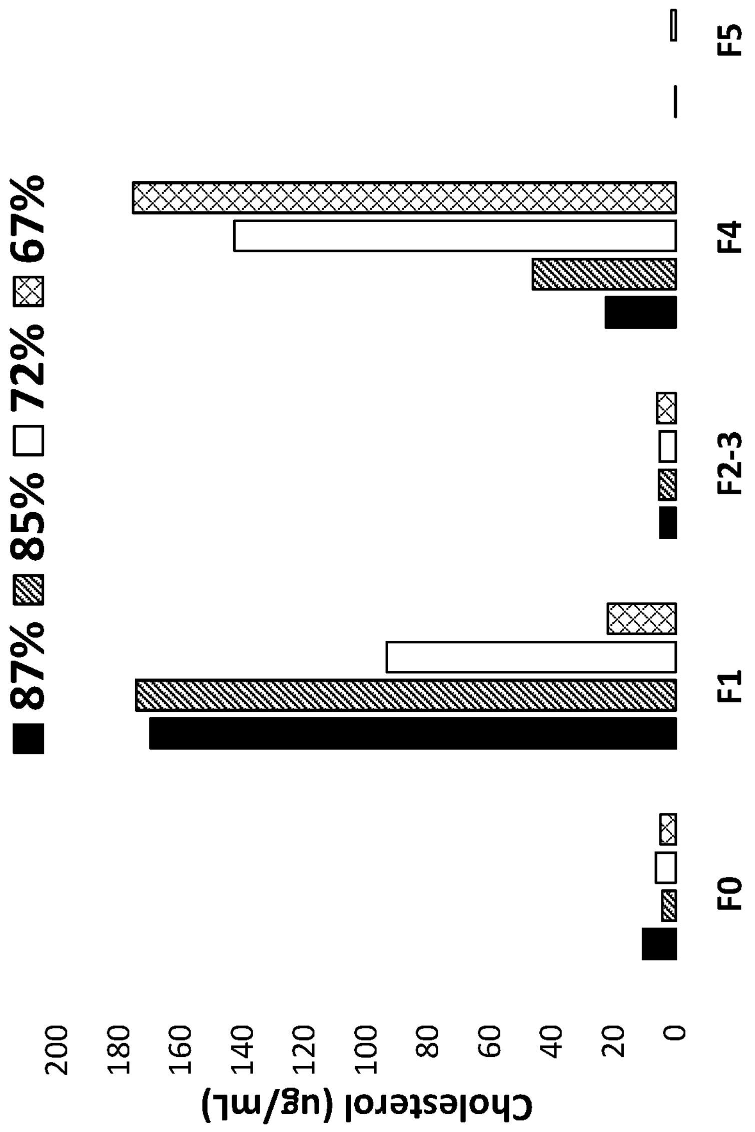
FIG. 7C shows cholesterol concentrations of each OPTIPREP™ fraction (e.g., F0-F5), from samples collected when cell viability was high (87% and 85%) and when cell viability was low (72% and 67%) (e.g., the dotted circles of FIG. 7A). Cholesterol was measured using AMPLEX®Red assay. Particle concentration was also measured using Nanoparticles Tracking Analysis (FIG. 7D).
Figure 7D:
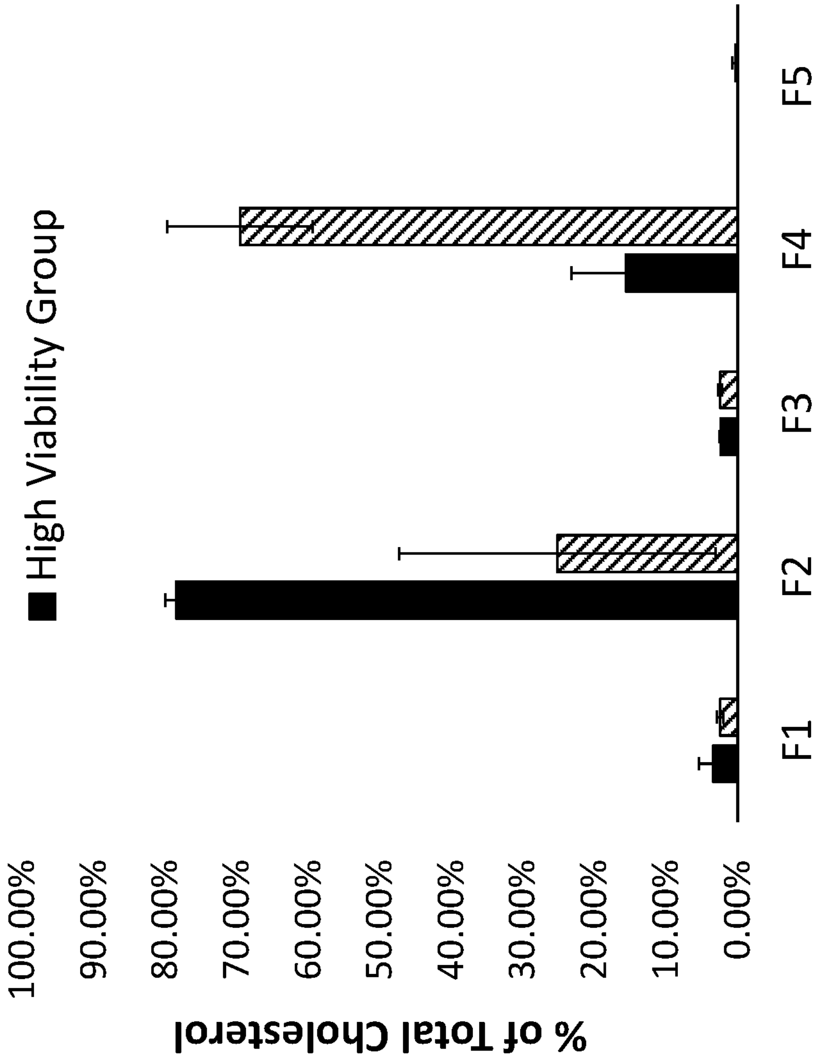

To determine the effect of cell culture viability on the accuracy of the cholesterol assay, exosomes from three groups of cells during a 9-day batch refeed experiment were isolated and their cholesterol concentration was analyzed. FIG. 7A shows the viability and viable cell density (VCD) of the three groups. For each group, a sample of cell-free culture medium was taken when cell viability was high (higher than 80%) and when cell viability was low (65-72%), and exosome isolation was performed using OPTIPREP™ density gradients (FIG. 7B). Cholesterol concentration of each Optiprep™ fraction, for groups with high and low cell viability was measured using the AMPLEX® Red assay (FIG. 7C). Particle concentration was also measured using Nanoparticles Tracking Analysis (FIG. 7D) and cholesterol/E11 particles is quantified in Table 6.

TABLE 6

| Cholesterol/E11 particles | High Viability Group | Low Viability Group |
|---|---|---|
| F0 | 15.49 | 16.29 |
| F1 | 10.70 | 10.96 |
| F2/3 | 9.80 | 6.23 |
| F4 | 4.83 | 12.70 |
| F5 | 0.01 | 2.18 |

Table 7 shows the amount of cholesterol in both the permeate as well as in the purified exosomes extracted from OPTIPREP™ methods at three different cell densities and cell viabilities. The effect of high and low cell viability on cholesterol measurements between the three culture conditions are shown (e.g., A, B, and C). At low viability, the cholesterol concentration in F1 fraction of OPTIPREP™ is lower, while in other OPTIPREP™ fractions, not representative of exosomes, the cholesterol content increased, suggesting a shift in particles attributes. Therefore the cholesterol assay may not be as accurate for titer measurement in lower viability samples.

TABLE 7

| | In PRM retains | | | After OPTIPREP ™ of 100 mL PRM | | |
|---|---|---|---|---|---|---|
| | Chol (μg/mL)-PRM | VCD E6cells/mL | Cell prod. (μg chol/E6 cells) | Chol. (μg/mL)-Opti | Particle density as measured by NTA | Viability (%) |
| A | 2.56 | 8 | 0.32 | 21.81 | 1.65E+11 | 66.8 |
| B | 2.38 | 11.3 | 0.21 | 169.82 | 1.59E+12 | 86.9 |
| C | 3.42 | 10.6 | 0.32 | 93.33 | 8.52E+11 | 71.7 |

Example 8

The average cholesterol (m)/E11 particles was compared between laboratory and GMP scale production runs for exosomes expressing PTGFRN and exosomes expressing PTGFRN fused to IL-12. Cells were cultured in perfusion or fed-batch bioreactors and EVs, e.g., exosomes, were isolated by OPTIPREP™ density gradients or chromatography. Average cholesterol (μg)/E11 particles are shown in Table 8.

TABLE 8

| | Average Cholesterol (μg)/E11 particles | | |
|---|---|---|---|
| | Lab Scale (Perfusion/Optiprep) | GMP Scale (Perfusion/Chromatography) | GMP Scale (Fed-batch/chromatography) |
| Wt-PTGFRN Exo | 8.7 | 4.5 | 3.9 |
| Wt PTGFRN -IL12 Exo | 8.2 | 7.9-9.1 | |

Table 8 shows the cholesterol content of purified exosomes expression prostaglandin F2 receptor negative regulator (PTGFRN) or PTGFRN-human IL-12 (hIL-12) as measured by AMPLEX® Red assay. Exosomes were produced in cell culture bioreactors either at the laboratory scale of 5 L or GMP scale of 500 L and 2000 L. Exosomes were either purified by Optiprep™, or by chromatography purification steps. The cholesterol content per particle content is relatively consistent, between 2.9-9 ug/E11 particles, as measured in two different types of engineered exosomes, produced under wide variety of conditions.

It is to be appreciated that the Detailed Description section, and not the Summary and Abstract sections, is intended to be used to interpret the claims. The Summary and Abstract sections can set forth one or more but not all exemplary aspects of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, can need to be revisited. Further, the Examiner is also reminded that any disclaimer made in the instant application should not be read into or against the parent application.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific aspects have been illustrated and described, the above specification is not restrictive. It will be appreciated that various changes can be made without departing from the spirit and scope of the disclosure(s).

The invention claimed is:

1. A method of quantifying a concentration of extracellular vesicles in a sample, comprising:

(i) providing a sample comprising one or more extracellular vesicles, wherein the extracellular vesicle is produced in a mixture comprising a cell, and wherein a cell viability of the mixture is at least about 72%;

(ii) processing the sample using filtration, ultracentrifugation, or polyethylene glycol (PEG) precipitation;

(iii) analyzing a cholesterol content of the sample using a fluorometric method to detect the cholesterol content, or wherein the cholesterol content is analyzed using a cholesterol assay kit; and (iv) correlating the cholesterol content of the sample with the concentration of extracellular vesicles.

2. The method of claim 1, wherein the sample is prepared from a bioreactor.

3. The method of claim 1, wherein the cell comprises a HEK293 cell, a Chinese hamster ovary (CHO) cell, a mesenchymal stem cell (MSC), a fibroblast cell, a s9f cell, a fHDF fibroblast cell, an AGE.HN neuronal precursor cell, a CAP amniocyte cell, a HT1080 cell, a C2C12 cell, a SIM-A9 cell, an adipose mesenchymal stem cell, an RPTEC/TERT1 cell, or any combination thereof.

4. The method of claim 1, wherein the cell viability is at least about 85%.

5. The method of claim 1, wherein:

(i) the sample is filtered using filtration or tangential flow filtration (TFF);

(ii) the sample is filtered using a 0.45 μm filter or a 0.2 μm filter; or (iii) the sample is prepared using sucrose gradient ultracentrifugation.

6. The method of claim 1, wherein:

(i) the cholesterol content is analyzed in cell culture;

(ii) a concentration of cholesterol analyzed is less than about 3000 μg/mL; or (iii) both (i) and (ii).

7. The method of claim 6, wherein the cholesterol content is analyzed in cell culture, and wherein:

(i) the cell culture is perfusion cell culture or fed-batch cell culture; or (ii) the cholesterol content is analyzed by collecting cellular supernatant at least once per day, for a period of about 1-90 days.

8. The method of claim 1, wherein the extracellular vesicles are engineered extracellular vesicles.

9. The method of claim 1, wherein the extracellular vesicles comprise a scaffold protein, wherein the scaffold protein is a Scaffold X protein or a Scaffold Y protein.

10. The method of claim 9, wherein the Scaffold X protein comprises prostaglandin F2 receptor negative regulator (PTGFRN); basigin (BSG); immunoglobulin superfamily member 2 (IGSF2); immunoglobulin superfamily member 3 (IGSF3); immunoglobulin superfamily member 8 (IGSF8); integrin beta-1 (ITGB1); integrin alpha-4 (ITGA4); 4F2 cell-surface antigen heavy chain (SLC3A2); a class of ATP transporter proteins; a functional fragment thereof; or any combination thereof.

11. The method of claim 9, wherein the Scaffold X protein comprises an amino acid sequence at least 90% identical to SEQ ID NO: 1.

12. The method of claim 9, wherein the Scaffold Y protein comprises myristoylated alanine rich Protein Kinase C substrate (MARCKS), myristoylated alanine rich Protein Kinase C substrate like 1 (MARCKSL1), brain acid soluble protein 1 (BASP1), a functional fragment thereof, or any combination thereof.

13. The method of claim 12, wherein the Scaffold Y comprises an N terminus domain (ND) and an effector domain (ED), wherein:

(i) the ND and/or the ED are associated with the luminal surface of the EV;

(ii) the ND is associated with the luminal surface of the extracellular vesicles via myristoylation;

(iii) the ED is associated with the luminal surface of the extracellular vesicles by an ionic interaction;

(iv) the ED comprises at least one basic amino acid in sequence, wherein the basic amino acid is selected from the group consisting of Lys, Arg, His, and any combination thereof;

or (v) any combination thereof.

14. The method of claim 13, wherein the basic amino acid is (Lys)n, wherein n is an integer between 1 and 10.

15. The method of claim 1, wherein the extracellular vesicles comprise:

(i) a protein, a peptide, a small molecule, a nucleotide, a polynucleotide, an oligonucleotide, a virus or any combination thereof; or (ii) an antibody or an antigen binding fragment thereof, a fusion protein, an oligonucleotide, a dinucleotide, an mRNA, a virus, or any combination thereof.

16. The method of claim 15, wherein the extracellular vesicles comprises:

(i) IL-2, IL-7, IL-12, CD40 L, FLT3 L, or any combination thereof;

(ii) an oligonucleotide targeting STAT3, STAT6, NRas, KRas, or CEBP/β;

(iii) a dinucleotide comprising a STING agonist; or (iv) any combination of (i) to (iii).

17. The method of claim 1, wherein the cholesterol content is compared to a reference nanoparticle tracking analysis (NTA) particle count curve to generate data sets comprising a cholesterol concentration standard curve and an NTA particle count curve, comparing the data sets generated by each curve, and correlating NTA particle counts to cholesterol concentrations.

18. The method of claim 1, wherein the extracellular vesicles are exosomes.

* * * * *